US012582461B2

(12) United States Patent
Rosa et al.

(10) Patent No.: US 12,582,461 B2
(45) Date of Patent: Mar. 24, 2026

(54) NEURAL ABLATION PROBE AND TEMPERATURE SENSING DEVICE AND RELATED SYSTEMS AND METHODS

(71) Applicant: NeuroOne Medical Technologies Corporation, Eden Prairie, MN (US)

(72) Inventors: Dave Rosa, Eden Prairie, MN (US); Camilo Diaz-Botia, Monte Sereno, CA (US); Samuel Ong, San Francisco, CA (US); Benjamin Lasota, Lubbock, TX (US); Christopher Blake Finnegan, Los Gatos, CA (US); Maria Vomero, Astoria, NY (US); Steve Mertens, Plymouth, MN (US); Timothy J. Kesti, Otsego, MN (US)

(73) Assignee: NEUROONE MEDICAL TECHNOLOGIES CORPORATION, Eden Prairie, MN (US)

( * ) Notice: Subject to any disclaimer, the term of this patent is extended or adjusted under 35 U.S.C. 154(b) by 292 days.

(21) Appl. No.: 18/468,087

(22) Filed: Sep. 15, 2023

(65) Prior Publication Data

US 2024/0090940 A1 Mar. 21, 2024

Related U.S. Application Data

(60) Provisional application No. 63/406,933, filed on Sep. 15, 2022.

(51) Int. Cl.
*A61B 18/14* (2006.01)
*A61B 18/00* (2006.01)

(52) U.S. Cl.
CPC ..................... *A61B 18/1482* (2013.01); *A61B 2018/00577* (2013.01); *A61B 2018/00797* (2013.01);
(Continued)

(58) Field of Classification Search
CPC ...... A61B 18/1482; A61B 2018/00577; A61B 2018/00797; A61B 2018/00815; A61B 2018/00821
See application file for complete search history.

(56) References Cited

U.S. PATENT DOCUMENTS 3,324,855 A     6/1967   Heimlich
4,158,916 A     6/1979   Adler
(Continued)

FOREIGN PATENT DOCUMENTS

EP          1870127 A1    12/2007
JP        2003500099 A     1/2003
(Continued)

OTHER PUBLICATIONS

International Searching Authority, "International Search Report and Written Opinion", From Application No. PCT/US2023/032880, Mailed Feb. 8, 2024, pp. 1-9.

*Primary Examiner* — Linda C Dvorak
*Assistant Examiner* — Abigail Bock
(74) *Attorney, Agent, or Firm* — Fredrikson & Byron, P.A.

(57) ABSTRACT

A system having an electrode probe and a temperature sensing device, wherein the temperature sensing device is positionable within the electrode probe. The probe can have an elongate electrode body, at least two electrode contacts disposed on the electrode body, and a lumen defined within the electrode body, and the temperature sensing device can have an elongate outer body having a lumen, an elongate inner sensing body disposed within the lumen, and at least one temperature sensor disposed on the elongate inner sensing body. The system in certain embodiments can also have a controller configured to receive temperature information from the temperature sensing device and use the
(Continued)

temperature information to adjust energy supply to at least one of the at least two electrode contacts.

20 Claims, 25 Drawing Sheets

(52) U.S. Cl.
CPC ............... *A61B 2018/00815* (2013.01); *A61B 2018/00821* (2013.01)

(56) References Cited

U.S. PATENT DOCUMENTS

| | | | |
|---|---|---|---|
| 4,946,457 | A | 8/1990 | Elliott |
| 5,606,974 | A | 3/1997 | Castellano et al. |
| 5,904,711 | A | 5/1999 | Flom et al. |
| 5,916,213 | A | 6/1999 | Haissaguerre et al. |
| 5,991,650 | A | 11/1999 | Swanson et al. |
| 6,205,361 | B1 | 3/2001 | Kuzma et al. |
| 6,415,187 | B1 | 7/2002 | Kuzma et al. |
| 7,337,012 | B2 | 2/2008 | Maghribi et al. |
| 7,387,626 | B2 | 6/2008 | Edwards et al. |
| 7,611,455 | B2 | 11/2009 | Borst et al. |
| 8,021,362 | B2 | 9/2011 | Deem et al. |
| 8,229,539 | B1 | 7/2012 | Motoyoshi et al. |
| 8,781,600 | B2 | 7/2014 | Janik et al. |
| 8,798,769 | B1 | 8/2014 | Parker, Jr. |
| 9,006,014 | B2 | 4/2015 | Mujeeb-U-Rahman et al. |
| 9,020,608 | B2 | 4/2015 | Swanson |
| 9,314,618 | B2 | 4/2016 | Imran et al. |
| 9,485,873 | B2 | 11/2016 | Shah et al. |
| 9,498,617 | B2 | 11/2016 | Shah et al. |
| 9,788,432 | B2 | 10/2017 | Greenberg et al. |
| 10,118,030 | B2 | 11/2018 | Pellinen et al. |
| 10,245,178 | B1 | 4/2019 | Heitzmann et al. |
| 2001/0011161 | A1* | 8/2001 | Edwards ................. A61N 1/06 604/22 |
| 2003/0078633 | A1 | 4/2003 | Firlik et al. |
| 2003/0124484 | A1 | 7/2003 | Reiz |
| 2003/0190608 | A1 | 10/2003 | Blackburn |
| 2004/0043479 | A1 | 3/2004 | Tuggle et al. |
| 2004/0186543 | A1 | 9/2004 | King et al. |
| 2005/0033286 | A1 | 2/2005 | Eggers et al. |
| 2005/0261673 | A1 | 11/2005 | Bonner et al. |
| 2006/0067649 | A1 | 3/2006 | Tung et al. |
| 2006/0129203 | A1 | 6/2006 | Garabedian et al. |
| 2006/0252014 | A1 | 11/2006 | Simon et al. |
| 2007/0073357 | A1 | 3/2007 | Rooney et al. |
| 2007/0088417 | A1 | 4/2007 | Schouenborg |
| 2007/0197892 | A1 | 8/2007 | Shen et al. |
| 2007/0287991 | A1 | 12/2007 | Mckay et al. |
| 2008/0039917 | A1 | 2/2008 | Cross et al. |
| 2008/0312716 | A1 | 12/2008 | Russell |
| 2009/0234426 | A1 | 9/2009 | Pellinen et al. |
| 2010/0114348 | A1 | 5/2010 | Boyden et al. |
| 2010/0152880 | A1 | 6/2010 | Boyden et al. |
| 2011/0034977 | A1 | 2/2011 | Janik et al. |
| 2011/0077660 | A1 | 3/2011 | Janik et al. |
| 2011/0130708 | A1 | 6/2011 | Perry et al. |
| 2011/0130805 | A1 | 6/2011 | Goel |
| 2011/0224682 | A1 | 9/2011 | Westlund et al. |
| 2012/0143296 | A1 | 6/2012 | Pianca et al. |
| 2013/0005169 | A1 | 1/2013 | Soltis et al. |
| 2013/0011332 | A1 | 1/2013 | Boyden et al. |
| 2013/0035574 | A1 | 2/2013 | Anand |
| 2013/0035660 | A1 | 2/2013 | Anand |
| 2013/0041445 | A1 | 2/2013 | Erickson et al. |
| 2013/0110210 | A1 | 5/2013 | North |
| 2013/0123775 | A1 | 5/2013 | Grunewald et al. |
| 2013/0165990 | A1 | 6/2013 | Mathur et al. |
| 2013/0238077 | A1 | 9/2013 | Feler |
| 2013/0289684 | A1 | 10/2013 | North et al. |
| 2013/0310823 | A1 | 11/2013 | Gelfand et al. |
| 2013/0312258 | A1 | 11/2013 | Swanson |
| 2014/0200511 | A1 | 7/2014 | Boyden et al. |
| 2014/0277317 | A1 | 9/2014 | Tooker et al. |
| 2014/0324117 | A1 | 10/2014 | Bedenbaugh |
| 2015/0032194 | A1 | 1/2015 | Mergen et al. |
| 2015/0045810 | A1 | 2/2015 | Hoffer et al. |
| 2015/0066105 | A1 | 3/2015 | Elborno |
| 2015/0066122 | A1 | 3/2015 | Govea |
| 2015/0094734 | A1 | 4/2015 | Staunton et al. |
| 2016/0000499 | A1 | 1/2016 | Lennox et al. |
| 2016/0038940 | A1 | 2/2016 | Babcock |
| 2016/0144189 | A1 | 5/2016 | Bakker et al. |
| 2017/0007813 | A1 | 1/2017 | Negi et al. |
| 2017/0173262 | A1 | 6/2017 | Veltz |
| 2017/0245772 | A1 | 8/2017 | Bierbrauer et al. |
| 2017/0246450 | A1 | 8/2017 | Liu et al. |
| 2017/0340891 | A1 | 11/2017 | Boggs et al. |
| 2018/0008821 | A1 | 1/2018 | Gonzalez et al. |
| 2018/0117313 | A1 | 5/2018 | Schmidt et al. |
| 2018/0126156 | A1 | 5/2018 | Sparks et al. |
| 2018/0289949 | A1 | 10/2018 | Bachinski et al. |
| 2018/0333571 | A1 | 11/2018 | Pepin et al. |
| 2019/0336771 | A1 | 11/2019 | Voit et al. |
| 2020/0008299 | A1 | 1/2020 | Tran et al. |
| 2020/0030024 | A1 | 1/2020 | Rao et al. |
| 2020/0091495 | A1 | 3/2020 | Ghezzi et al. |
| 2020/0107743 | A1 | 4/2020 | Bachinski et al. |
| 2020/0281489 | A1 | 9/2020 | Rosa et al. |
| 2020/0391027 | A1 | 12/2020 | Thakkar et al. |
| 2021/0008364 | A1 | 1/2021 | Chen et al. |
| 2021/0046305 | A1 | 2/2021 | Rosa et al. |
| 2021/0101010 | A1 | 4/2021 | Howard et al. |

FOREIGN PATENT DOCUMENTS

| | | | |
|---|---|---|---|
| WO | 2014113612 | A1 | 7/2014 |
| WO | 2021021886 | A1 | 2/2021 |

* cited by examiner

| RF Generator | | Generator Interface Cable | | RF Connector Box (RFCB) | |
| Stand / Cart | | | | | |
| Foot Pedal | | | | | |

12

18

12

18

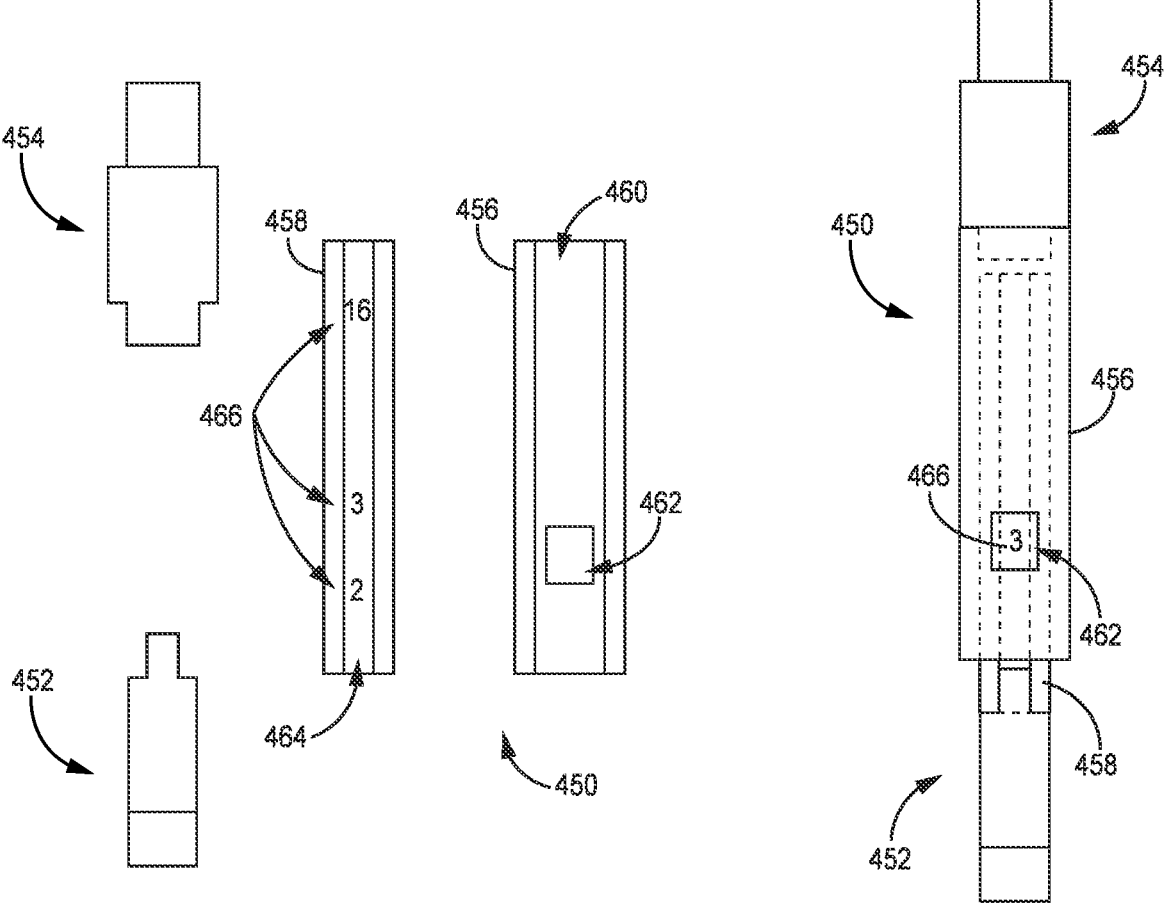
FIG. 22A                    FIG. 22B

470

476

472

474

NEURAL ABLATION PROBE AND TEMPERATURE SENSING DEVICE AND RELATED SYSTEMS AND METHODS

CROSS-REFERENCE TO RELATED APPLICATION(S)

This application claims the benefit under 35 U.S.C. § 119(e) to U.S. Provisional Application 63/406,933, filed Sep. 15, 2022 and entitled "Neural Ablation Probe and Temperature Sensing Device and Related Systems and Methods," which is hereby incorporated herein by reference in its entirety.

FIELD

The various embodiments herein relate to neural and spinal cord electrode devices and systems, including such devices and related methods that involve the use or can benefit from the use of temperature sensing technologies.

BACKGROUND

Certain known neural and spinal probes and related devices utilize thin film, flexible printed circuits, offering thinner and more flexible products compared to current electrodes. The use of flexible printed circuits may also allow for increased product consistency and decreased production delays.

Certain probes can include a temperature sensor therein. However, it is difficult to incorporate a temperature sensor into certain types of probes, including sEEG depth electrodes for neural implantation. That is, typical sEEG depth electrodes are generally constructed such that only recording and stimulating components can be incorporated therein. As a result, such devices typically do not have any temperature sensing capabilities.

There is a need in the art for improved thin film ablation probes in combination with a temperature sensing device and related systems and methods.

BRIEF SUMMARY

Discussed herein are various systems and devices that include both an elongate electrode device and a temperature sensing device that can be positioned within the electrode device.

In Example 1, a an electrode probe and temperature sensor system comprises an electrode device and a temperature sensing device. The electrode device comprises an elongate tubular electrode body, the tubular electrode body comprising at least two electrode contacts disposed on the elongate tubular electrode body, a first lumen defined within the elongate tubular electrode body, and a proximal opening disposed near a proximal end of the elongate tubular electrode body, wherein the proximal opening is in fluidic communication with the first lumen. The temperature sensing device is sized to be positionable within the first lumen and comprises an elongate outer body comprising a second lumen defined within the elongate outer body, an elongate inner sensing body disposed within the second lumen, and a first temperature sensor disposed on the elongate inner sensing body.

Example 2 relates to the system according to Example 1, wherein the temperature sensing device further comprises a distal tip disposed at or near a distal end of the elongate outer body.

Example 3 relates to the system according to Example 2, wherein at least a portion of the distal tip is disposed within the second lumen.

Example 4 relates to the system according to Example 2, wherein at least a portion of the distal tip is disposed around the elongate outer body.

Example 5 relates to the system according to Example 1, further comprising a controller operably coupled to the electrode device and the temperature sensing device, wherein the controller is configured to receive temperature information from the temperature sensing device and use the temperature information to adjust energy supply to at least one of the at least two electrode contacts.

Example 6 relates to the system according to Example 1, wherein the temperature sensing device is positionable within the first lumen such that the first temperature sensor is disposed in proximity with one of the at least two electrode contacts.

Example 7 relates to the system according to Example 1, wherein the temperature sensing device comprises a second temperature sensor disposed on the elongate inner sensing body.

Example 8 relates to the system according to Example 1, further comprising at least one spacing device removably coupleable at a first end with the proximal end of the elongate tubular electrode body and at a second end with the temperature sensing device.

In Example 9, an electrode probe and temperature sensor system comprises an electrode device comprising an elongate tubular electrode body and a temperature sensing device. The tubular electrode body comprises at least two electrode contacts disposed on the elongate tubular electrode body, a first lumen defined within the elongate tubular electrode body, and a proximal opening disposed near a proximal end of the elongate tubular electrode body, wherein the proximal opening is in fluidic communication with the first lumen. The temperature sensing device is sized to be positionable within the first lumen and comprises an elongate core body and a thin film body disposed around the elongate core body. The thin film body comprises an elongate base, at least two temperature sensors disposed on a top surface of the elongate base, an elongate common trace disposed on the top surface of the elongate base, wherein the elongate common trace is electrically coupled to the at least two temperature sensors, and at least two elongate separate traces disposed on a bottom surface of the elongate base, wherein each of the at least two elongate separate traces is electrically coupled to one of the at least two temperature sensors.

Example 10 relates to the system according to Example 9, wherein the thin film body further comprises at least two vias disposed through the elongate base, wherein each of the two vias electrically couples one of the at least one temperature sensors to one of the at least two elongate separate traces.

Example 11 relates to the system according to Example 9, wherein the thin film body is a thin film ribbon disposed around the elongate core body in a helical configuration.

In Example 12, an ablation system comprises an ablation device, a temperature sensing device, at least one spacing device removably coupleable at a first end with the ablation device and at a second end with the temperature sensing device, and a controller operably coupled to the electrode device and the temperature sensing device. The ablation device comprises an elongate electrode body, at least two electrode contacts disposed on the elongate electrode body, and a first lumen defined within the elongate electrode body.

The temperature sensing device is sized to be positionable within the first lumen and comprises an elongate outer body comprising a second lumen defined within the elongate outer body, an elongate inner sensing body disposed within the second lumen, and at least one temperature sensor disposed on the elongate inner sensing body, wherein the temperature sensing device is positionable within the first lumen such that the at least one temperature sensor is disposed in proximity with one of the at least two electrode contacts. Further, the controller is configured to receive temperature information from the temperature sensing device and use the temperature information to adjust energy supply to at least one of the at least two electrode contacts.

Example 13 relates to the system according to Example 12, wherein the temperature sensing device comprises at least two temperature sensors disposed on the elongate inner sensing body.

Example 14 relates to the system according to Example 12, wherein the at least one spacing device comprises an elongate tubular spacing body, a spacing device lumen defined within the elongate tubular spacing body, and an elongate opening defined along a length of the elongate tubular spacing body, wherein the elongate opening is in fluidic communication with the spacing device lumen, wherein the at least one spacing device is attachable to and detachable from the temperature sensing device via the elongate opening.

Example 15 relates to the system according to Example 12, wherein the at least one spacing device comprises an adjustable spacing device.

Example 16 relates to the system according to Example 15, wherein the adjustable spacing device comprises and elongate tubular spacing body and an elongate tubular insert body. The elongate tubular spacing body comprises a spacing body lumen defined within the elongate tubular spacing body, an opening defined in the elongate tubular spacing body, wherein the opening is in visual communication with the spacing body lumen, and an end of the elongate tubular spacing body coupleable with the temperature sensing device such that the elongate tubular spacing body is axially constrained to the temperature sensing device. The elongate tubular insert body is slidably disposed within the spacing body lumen and comprises an insert body lumen defined within the elongate tubular insert body, a plurality of markings on an external surface of the elongate tubular insert body such that the plurality of markings are visible through the opening defined in the elongate tubular spacing body, and an end of the elongate tubular insert body coupleable with the ablation device such that the elongate tubular insert body is axially constrained to the ablation device.

Example 17 relates to the system according to Example 12, wherein the at least one spacing device comprises a plurality of spacing devices, wherein each of the plurality of spacing devices has a different length in comparison to every other of the plurality of spacing devices, wherein a desired spacing device can be selected from the plurality of the spacing devices such that the at least one temperature sensor is disposed in proximity with a desired one of the at least two electrode contacts.

Example 18 relates to the system according to Example 12, wherein the elongate electrode body comprises a proximal support body disposed at a proximal end of the elongate electrode body, the proximal support body comprising a support body lumen in fluidic communication with the first lumen.

Example 19 relates to the system according to Example 18, wherein the ablation device further comprises a proximal tail extending from the proximal support body.

Example 20 relates to the system according to Example 18, wherein the at least one spacing device is removably coupleable at the first end with a proximal end of the proximal support body.

While multiple embodiments are disclosed, still other embodiments will become apparent to those skilled in the art from the following detailed description, which shows and describes illustrative embodiments. As will be realized, the various implementations are capable of modifications in various obvious aspects, all without departing from the spirit and scope thereof. Accordingly, the drawings and detailed description are to be regarded as illustrative in nature and not restrictive.

BRIEF DESCRIPTION OF THE DRAWINGS

FIG. 22A is an exploded view of an adjustable spacing device, according to one embodiment.

FIG. 22B is a top view of the adjustable spacing device coupled to an electrode device and a temperature sensing device, according to one embodiment.

DETAILED DESCRIPTION

Figure 1A:
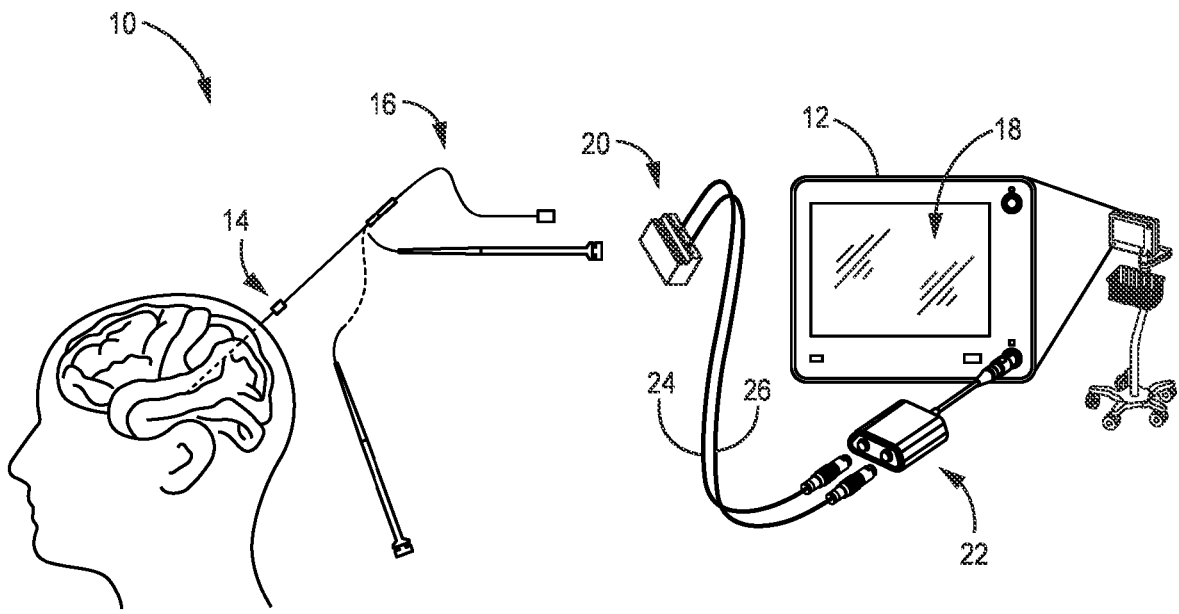
FIG. 1A is a schematic view of a system that includes both an electrode device and a temperature sensing device, according to one embodiment.

The various embodiments herein relate to a tissue recording and ablation system with temperature feedback and power modulation. In certain specific implementations, a tissue ablation system is provided that has an ablation electrode, a temperature sensing device, and a controller to collect temperature feedback from the temperature sensing device and use that feedback to control the energy delivered to the ablation electrode. In addition, some embodiments relate to a temperature sensing device that can be used in combination with any known ablation electrode for localized sensing of temperature at each electrode contact. Further, certain implementations relate to a multifunctional neural or spinal probe capable of recording electrical activity, ablation, and acute or chronic stimulation combined with a temperature sensing device for localized sensing of temperature at each probe contact. The various electrode embodiments herein can be used independently or in combination with other diagnostic systems such as MRI systems or the like. The various electrode implementations can be placed percutaneously or via any surgical approach. The electrical contacts on any of the embodiments can have various shapes and/or sizes to accommodate a patient's specific anatomy.

One advantage of certain embodiments herein is the incorporation of temperature sensing capabilities into certain types of neural probe devices, including sEEG depth electrodes, by providing a separate temperature sensing device that can be used in conjunction with a neural probe device. According to some implementations, such systems can be used for not only recording and stimulation, but also ablation.

One embodiment of an ablation electrode and temperature sensing device system 10 is depicted in FIGS. 1A-1D. The system 10 has a controller 12 that is coupled to an ablation probe 14 and a temperature sensing device 16. In certain embodiments, the controller 12 has a radiofrequency generator 28 (as best shown schematically in FIG. 1B) that provides the ablation energy to the ablation probe 14 and has an interactive interface 18 on the controller 12 that is accessible to a user during operation.

Figure 1B:
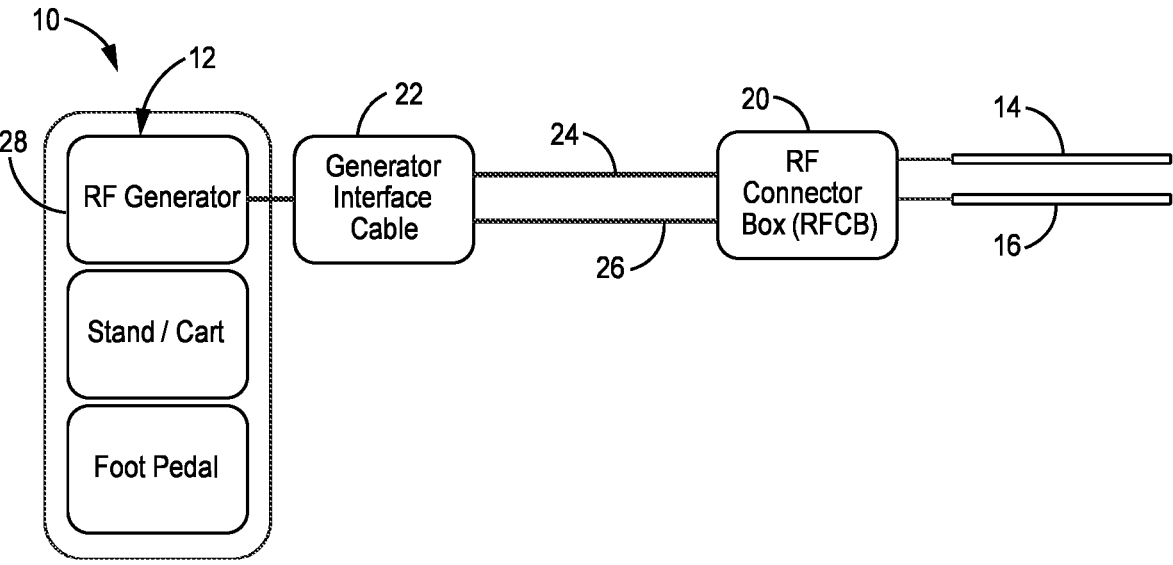
FIG. 1B is a schematic block summary of the system of FIG. 1A, according to one embodiment.

As shown in FIGS. 1A and 1B, in certain implementations, the system 10 provides for the controller 12 to be coupled to the ablation probe 14 and temperature sensing device 16 in the following, non-limiting manner. The system 10 can have a connector box 20 to which the probe 14 and device 16 are coupled and further can have a controller interface box 22 coupled to the controller 12, with the connector box 20 and the interface box 22 coupled via first and second cables 24, 26 as shown. Two cables 24, 26 are provided in this exemplary embodiment because each cable 24, 26 corresponds to one contact on the ablation probe 14. Thus, in those embodiments in which the probe 14 has two active contacts, there are two cables 24, 26 with one cable 24 coupled to a first of the two contacts (via the connector box 20) and the second cable 26 coupled to the second of the two contacts (via the connector box 20). Thus, in this exemplary embodiment, the first cable 24 can contain conductors to carry the signals from the temperature sensing device 16 and related components and the radio frequency signal corresponding to the first active contact on the ablation probe 14. Further, the second cable 26 can contain a conductor to carry the signals from the temperature sensing device 16 and related components and the radio frequency signal corresponding to the second active contact on the ablation probe 14. Alternatively, any coupling mechanisms, cables, and features can be used to couple the controller 12 to the ablation probe 14 and the temperature sensing device 16. Further, according to certain embodiments in which there is only one active contact on the ablation probe 14, only one of the two cables 24, 26 is used or needed.

The ablation probe 14, according to one embodiment, is a radiofrequency ("RF") ablation probe 14. In certain exemplary embodiments, the RF ablation probe 14 has thin film components, as will be described in additional detail below. Alternatively, the RF ablation probe 14 can be any known RF ablation probe 14. In a further alternative, the ablation probe 14 can be any known ablation probe 14. According to various implementations, the ablation probe is an SEEG electrode probe.

Figure 1C:
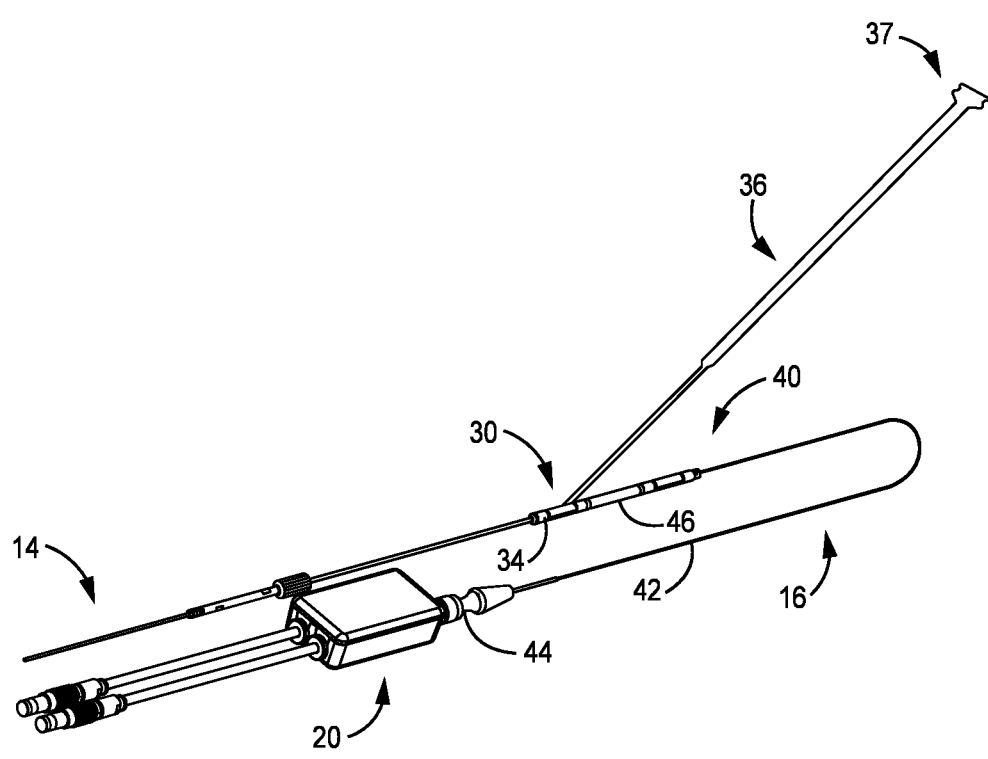
FIG. 1C is a perspective view of an electrode device with a temperature sensing device coupled thereto, according to one embodiment.
Figure 1D:
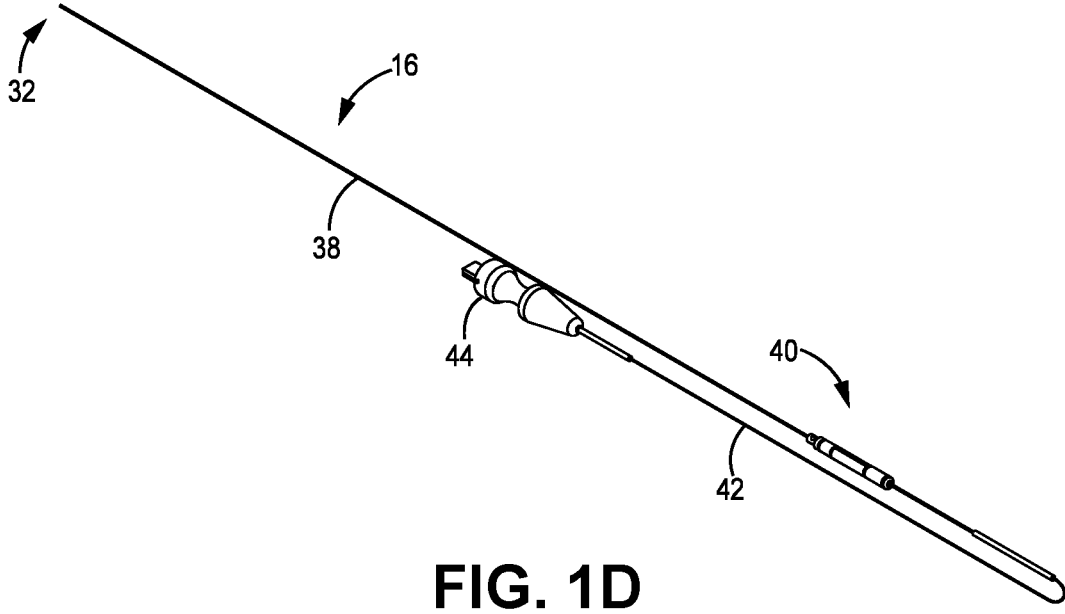
FIG. 1D is a perspective view of the temperature sensing device of FIG. 1C, according to one embodiment.

One specific implementation of the ablation probe 14 with the temperature sensing device 16 disposed therein is depicted in FIG. 1C, while the temperature sensing device 16 alone is depicted in FIG. 1D. The ablation probe 14 has a support structure 34 at the proximal end 30 that is provided to strengthen/reinforce the proximal end 30. Another exemplary embodiment of a support structure 308 will be described in additional detail below in relation to FIGS. 18A, 18C, and 18D. The structure 34 can have an opening (not shown) at the proximal end thereof such that the distal end 32 of the temperature sensing device 16 is inserted therethrough as shown. Further, the tail 36 of the probe 14 extends proximally from the strain relief structure 34 as shown, with the proximal connector 37 disposed at the proximal end of the tail 36. The proximal connector 37 is coupleable with the connector box 20 as discussed above. Alternatively, the proximal connector 37 can be coupleable to an intermediate cable (not shown) that couples to the connector box 20. The temperature sensing device 16 has an elongate body 38 with a connection (or "probe attachment") mechanism 40 disposed at or near a proximal end of the body 38. Further, the device 16 has an extension body 42 that extends proximally from the connection mechanism 40 with a connector 44 disposed at the proximal end of the extension body 42 that can be coupled to the connector box 20 by inserting the connector 44 into a port (not shown) thereof. According to one embodiment, the extension body 42 can be a tube 42 that provides additional support and strength to the temperature sensing device 16, especially the internal components of the device 16. For example, in those temperature sensing device embodiments having a temperature sensing apparatus (such as any of the apparatuses 62, 82, 122, 142), the tube 42 can help to provide protection for that apparatus from strain resulting from flexing or pulling the device 16. According to one embodiment, the tube 42 is a polyimide tube 42. Alternatively, the tube 42 can be made of polyurethane, polypropylene, polyethylene, or any other known polymeric material that can be used in such a tube.

In addition, as best shown in FIG. 1C, the system can also have a spacing device (or "spacer") 46 disposed between the proximal end 30 of the probe 14 and the connection mechanism 40 of the temperature sensing device 16. As will be discussed in additional detail below, the spacer 46 can be used to position the temperature sensing device 16 in a specific position in relation to the probe 14 and thereby ensure that the temperature sensor (not shown) of the device 16 is disposed in the desired location in relation to a contact (not shown) of the probe 14.

In general, the various system 10 embodiments disclosed or contemplated herein can be used in the following manner, with reference to FIGS. 1C and 1D. First, the ablation probe 14 (or any known ablation electrode/probe) is inserted into the brain of the patient and positioned as desired. Prior to ablation, the temperature sensing device 16 (with the spacer 46 attached) is inserted into the lumen (not shown) in the ablation probe 14. More specifically, the distal end 32 of the temperature sensing device 16 is inserted through the opening (not shown) in the proximal end 40 of the ablation probe 14 and urged distally through the lumen (not shown) in the ablation probe 14. As such, when the temperature sensing device 16 is fully disposed within the ablation probe 14 (as shown in FIG. 1C), each of the one or more temperature sensors (as discussed in detail below) on the temperature sensing device 16 is positioned adjacent to or in close proximity to an electrode contact (not shown) on the probe 14 such that the temperature of that contact can be detected by the temperature sensing device 16. During use of the ablation probe 14, this contact-specific temperature information can be transmitted to the controller 12 and utilized by the controller 12 to control the energy transmitted to that specific contact (not shown) based on that temperature information. Thus, the system 10 provides for temperature feedback during ablation and real-time adjustment of the ablation energy based on that feedback.

Figure 2A:
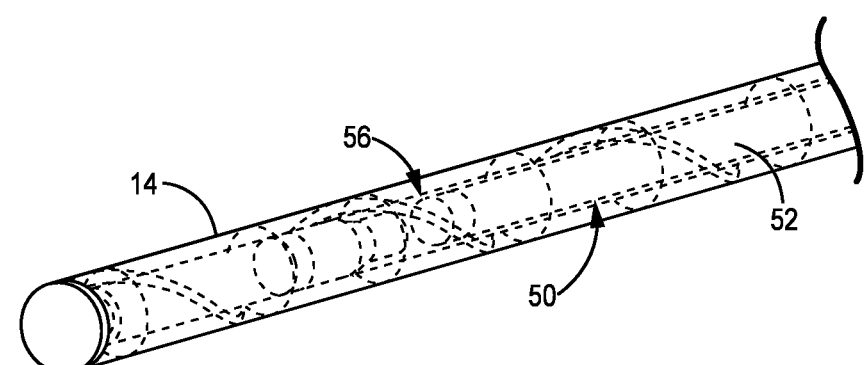
FIG. 2A is a perspective view of an electrode device with a temperature sensing device disposed therein, according to one embodiment.
Figure 2B:
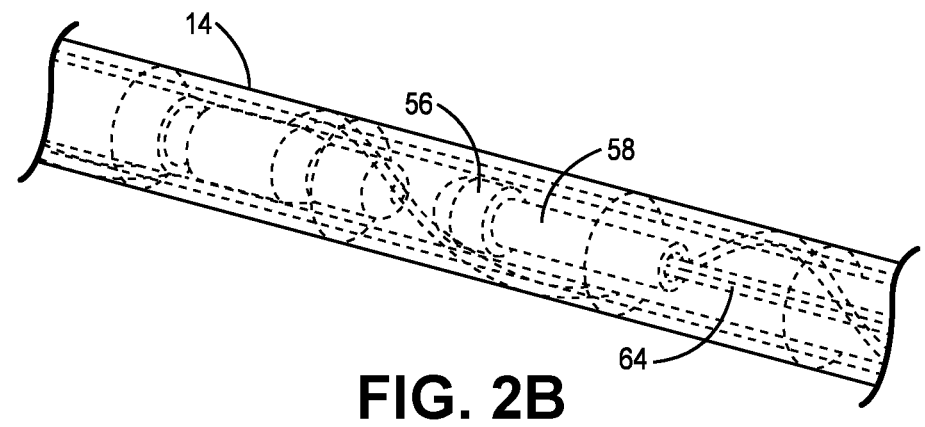
FIG. 2B is a different, enlarged perspective view of the electrode device with the temperature sensing device disposed therein of FIG. 2A, according to one embodiment.
Figure 2C:
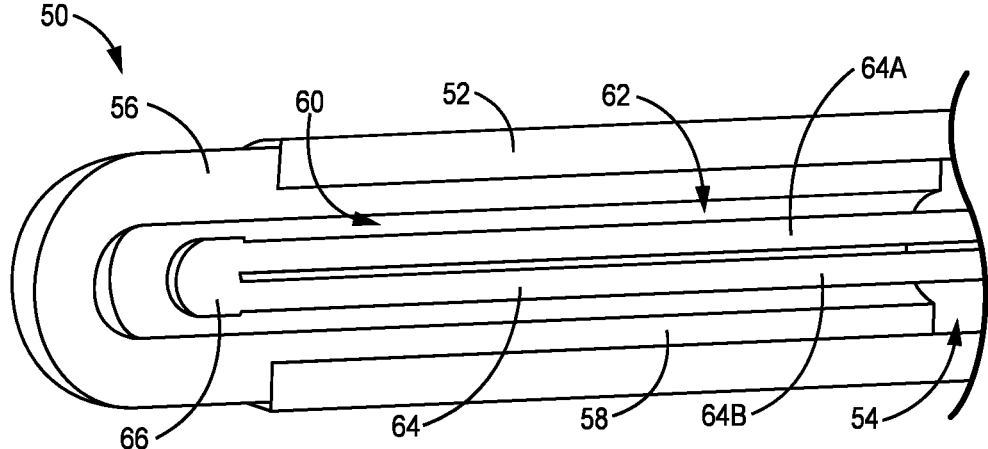
FIG. 2C is an enlarged cross-sectional perspective view of the distal end of the temperature sensing device of FIG. 2A, according to one embodiment.

One specific implementation of a temperature sensing device 50 is depicted in FIGS. 2A-2C. More specifically, FIGS. 2A and 2B show the device 50 disposed within an ablation probe 14, while FIG. 2C depicts the distal end of the device 50. The device 50 has an elongate body 52 with a lumen 54 defined therein, a tip 56 attached to the distal end of the body 52 with a tip body 58 (with a lumen 60 defined therein) that is positioned within a distal portion of the lumen 54, and a temperature sensing apparatus 62 disposed within the lumen 54 of the body 52 such that the distal end of the temperature sensing apparatus 62 extends into the lumen 60 of the tip 56. The temperature sensing apparatus 62 has an elongate body 64 and a temperature sensor 66 disposed at the distal end. In this specific embodiment, temperature sensing apparatus body 64 is two elongate wires 64A, 64B and the temperature sensor 66 is a thermocouple 66 formed at the distal end of the two wires 64A, 64B. Alternatively, the temperature sensor 66 can be any known form or type of temperature sensor 66.

In accordance with one embodiment, the elongate body 52 of the temperature sensing device 50 is made of polyimide. Alternatively, the body 52 can be made of liquid crystal polymer, Teflon®, polypropylene, or any other known material having substantially similar mechanical properties as polyimide. In certain implementations, the tip 56 and tip body 58 can be made of titanium, stainless steel, platinum, aluminum, gold, or any other material having similar mechanical properties. According to some embodiments, the wires 64A, 64B and sensor 66 can be made of copper, nickel, constantan, iron, chromium, platinum, rhodium, iridium, their alloys, or any other material having substantially similar electrical conduction properties. The temperature sensing apparatus 62, in accordance with certain aspects, can be positioned within the lumens 54, 60 with an epoxy or other known filling material with similar properties such that the temperature sensing apparatus 62 is positioned as desired.

The elongate body 52 can have a diameter ranging from about 100 μm to about 2 mm, while the lumen 54 defined within the body 52 can have an inner diameter ranging from about 75 μm to about 1.95 mm. The head of the tip 56 can have a diameter ranging from about 100 μm to about 2 mm, while the tip body 58 can have a diameter ranging from about 65 μm to about 1.9 mm, and the tip lumen 60 can have an inner diameter ranging from about 50 μm to about 1.8 mm. In some implementations, the tip 56 and tip body 58 can have a length ranging from about 0.5 mm to about 5 mm. In addition, the device 50 can have a length ranging from about 10 cm to about 1 m.

Figure 3A:
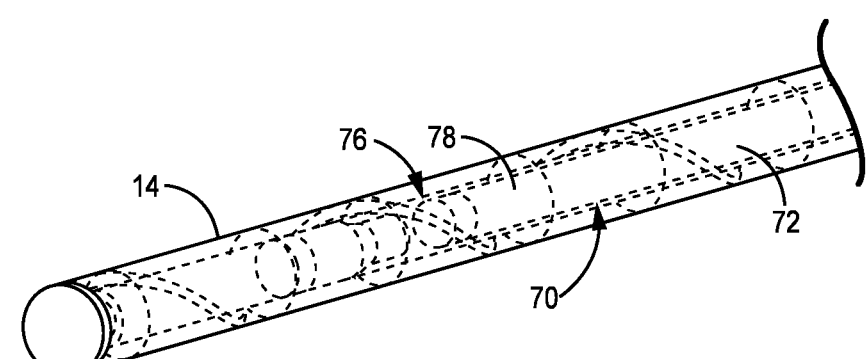
FIG. 3A is a perspective view of an electrode device with a temperature sensing device disposed therein, according to another embodiment.
Figure 3B:
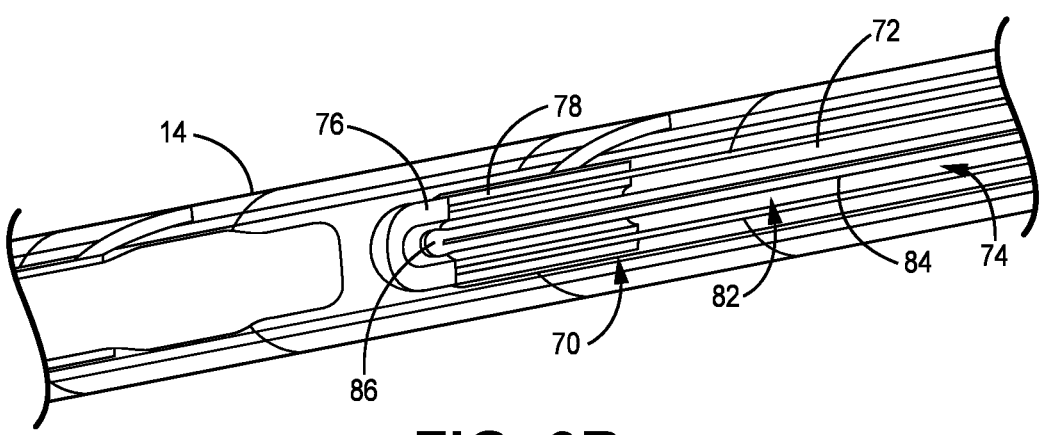
FIG. 3B is an enlarged cross-sectional perspective view of the electrode device with the temperature sensing device disposed therein of FIG. 3A, according to one embodiment.
Figure 3C:
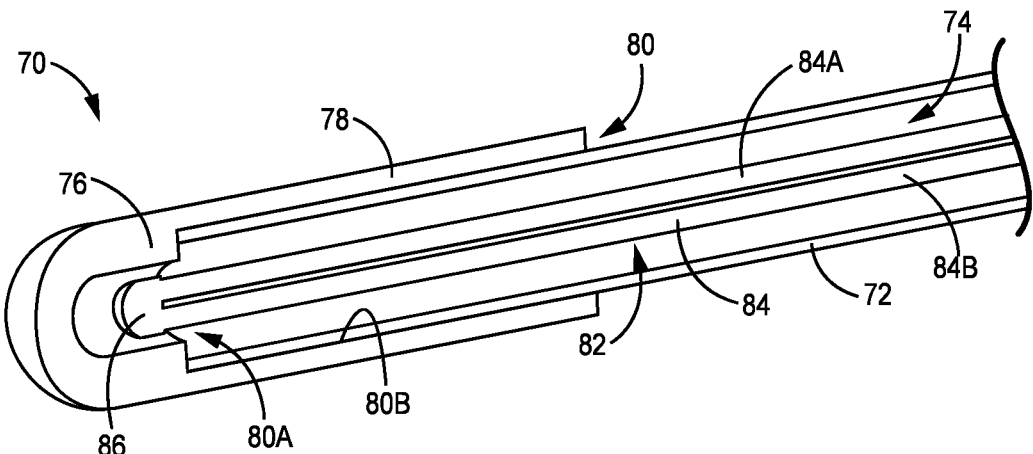
FIG. 3C is an enlarged cross-sectional perspective view of the distal end of the temperature sensing device of FIG. 3A, according to one embodiment.

Another temperature sensing device embodiment 70 is depicted in FIGS. 3A-3C. More specifically, FIGS. 3A and 3B show the device 70 disposed within an ablation probe 14, while FIG. 3C depicts the distal end of the device 70. The device 70 has an elongate body 72 with a lumen 74 defined therein, a tip 76 attached to the distal end of the body 72 with a tip body 78 (with a lumen 80 defined therein) that is positioned over a distal portion of the elongate body 72 (such that the elongate body 72 is disposed within the lumen 80), and a temperature sensing apparatus 82 disposed within the lumen 74 of the body 72 such that the distal end of the temperature sensing apparatus 82 extends into the lumen 80 of the tip 76. Further, in this specific embodiment, the lumen 80 of the tip body 78 has two different sections 80A, 80B with different inner diameters: a distal section 80A and a proximal section 80B with a larger inner diameter than the distal section 80A. Thus, the proximal section 80B is sized to receive the distal end of the elongate body 72, while the distal section 80A is sized to allow for the distal end of the temperature sensing apparatus 82 to be disposed therein as shown. The temperature sensing apparatus 82 has an elongate body 84 and a temperature sensor 86 disposed at the distal end. In this specific embodiment, the temperature sensing apparatus body 84 is two elongate wires 84A, 84B and the temperature sensor 86 is a thermocouple 86 formed at the distal end of the two wires 84A, 84B. Alternatively, the temperature sensor 86 can be any known form or type of temperature sensor 86.

In accordance with one embodiment, the elongate body 72 of the temperature sensing device 70 is made of polyimide. Alternatively, the body 72 can be made of liquid crystal polymer, Teflon®, polypropylene, or any other known material having substantially similar mechanical properties as polyimide. In certain implementations, the tip 76 and tip body 78 can be made of titanium, stainless steel, platinum, aluminum, gold, or any other material having similar mechanical properties. According to some embodiments, the wires 84A, 84B and sensor 86 can be made of copper, nickel, constantan, iron, chromium, platinum, rhodium, iridium, their alloys, or any other material having substantially similar electrical conduction properties. The temperature sensing apparatus 82, in accordance with certain aspects, can be positioned within the lumens 74, 80 with an epoxy or other known filling material with similar properties such that the temperature sensing apparatus 82 is positioned as desired.

The elongate body 72 can have a diameter ranging from about 100 μm to about 2 mm, while the lumen 74 can have an inner diameter ranging from about 75 μm to about 1.95 mm. The head of the tip 76 can have a diameter ranging from about 125 μm to about 2.1 mm, while the tip body 78 can have a diameter ranging from about 125 μm to about 2.1 mm. And the distal section 80A of the tip lumen 80 can have an inner diameter ranging from about 75 μm to about 1.95 mm, while the proximal section 80B of the tip lumen 80 can have an inner diameter ranging from about 110 μm to about 2.05 mm. In some implementations, the tip 76 and tip body 78 can have a length ranging from about 0.5 mm to about 5 mm. In addition, the device 70 can have a length ranging from about 10 cm to about 1 m.

Figure 4A:
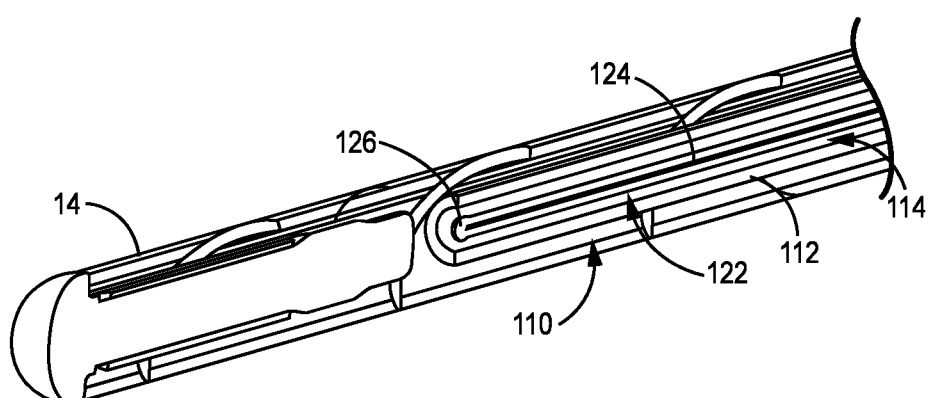
FIG. 4A is a perspective view of an electrode device with a temperature sensing device disposed therein, according to a further embodiment.
Figure 4B:
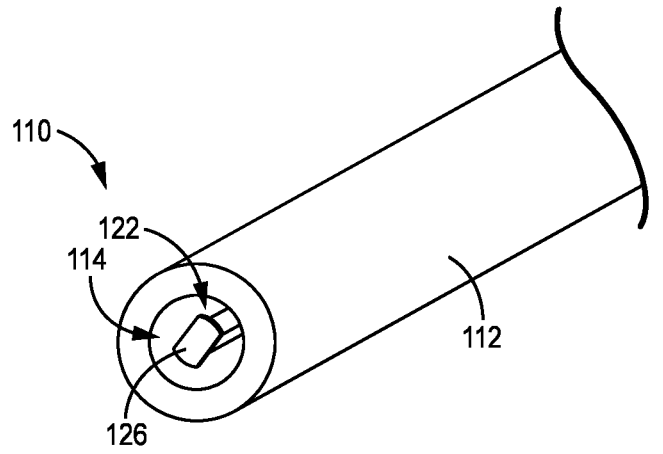
FIG. 4B is an enlarged perspective view of the distal end of the temperature sensing device of FIG. 4A, according to one embodiment.
Figure 4C:
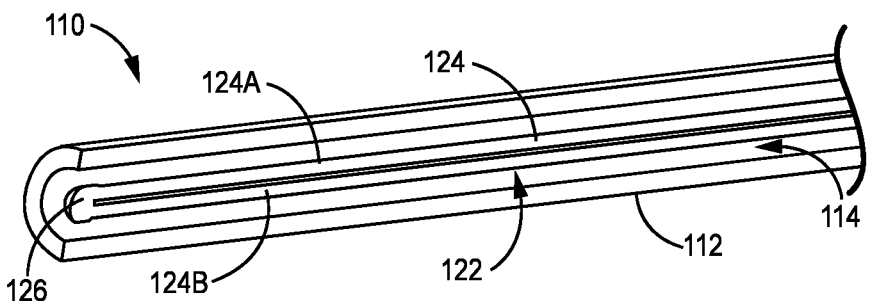
FIG. 4C is an enlarged cross-sectional perspective view of the distal end of the temperature sensing device of FIG. 4A, according to one embodiment.

A further temperature sensing device implementation 110 is depicted in FIGS. 4A-4C. More specifically, FIG. 4A shows the device 110 disposed within an ablation probe 14, while FIGS. 4B and 4C depict the distal end of the device 110. The device 110 has an elongate body 112 that is a hypotube 112 with a lumen 114 defined therein, and a temperature sensing apparatus 122 disposed within the lumen 114 of the hypotube 112. The temperature sensing apparatus 122 has an elongate body 124 and a temperature sensor 126 disposed at the distal end. In this specific embodiment, the temperature sensing apparatus body 124 is two elongate wires 124A, 124B and the temperature sensor 126 is a thermocouple 126 formed at the distal end of the two wires 124A, 124B. Alternatively, the temperature sensor 126 can be any known form or type of temperature sensor 126.

In accordance with one embodiment, the elongate body 112 of the temperature sensing device 110 is made of stainless steel, platinum, aluminum, gold, nickel, or any other known material having substantially similar mechanical properties. As such, the elongate body 112 is less flexible (or more rigid) than the elongate bodies 52, 72, 92 discussed in detail above. According to some embodiments, the wires 124A, 124B and sensor 126 can be made of copper, nickel, constantan, iron, chromium, platinum, rhodium, iridium, their alloys, or any other material having substantially similar electrical conduction properties. The temperature sensing apparatus 122, in accordance with certain aspects, can be positioned within the lumen 114 with an epoxy or other known filling material with similar properties such that the temperature sensing apparatus 122 is positioned as desired. Further, the elongate body 124 and the sensor 126 can have a coating or layer attached thereto that can encapsulate the non-biocompatible materials that make up the body 124 and sensor 126 and help to prevent corrosion/oxidation of the sensor 126. According to one embodiment, the coating can be a polymeric coating that is made of parylene, polyimide, Teflon, or any other polymeric material that can be used for such a coating.

The elongate body 112 can have a diameter ranging from about 100 µm to about 2 mm, while the lumen 114 can have an inner diameter ranging from about 75 µm to about 1.95 mm. In addition, the device 110 can have a length ranging from about 10 cm to about 1 m.

Figure 5A:
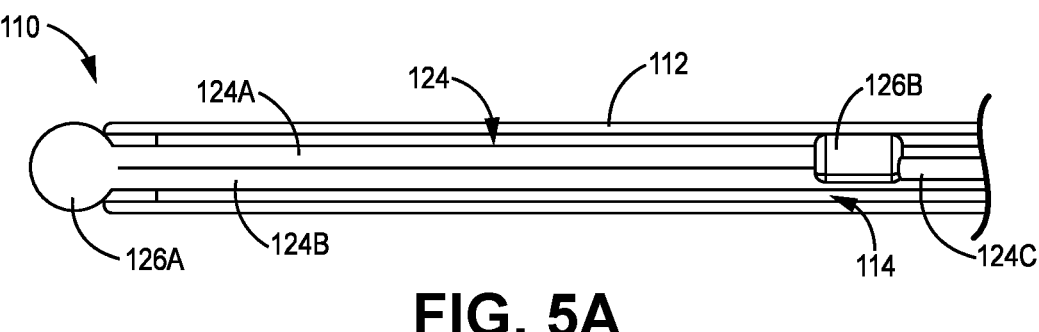
FIG. 5A is a cross-sectional perspective view of a temperature sensing device, according to yet another embodiment.
Figure 5B:
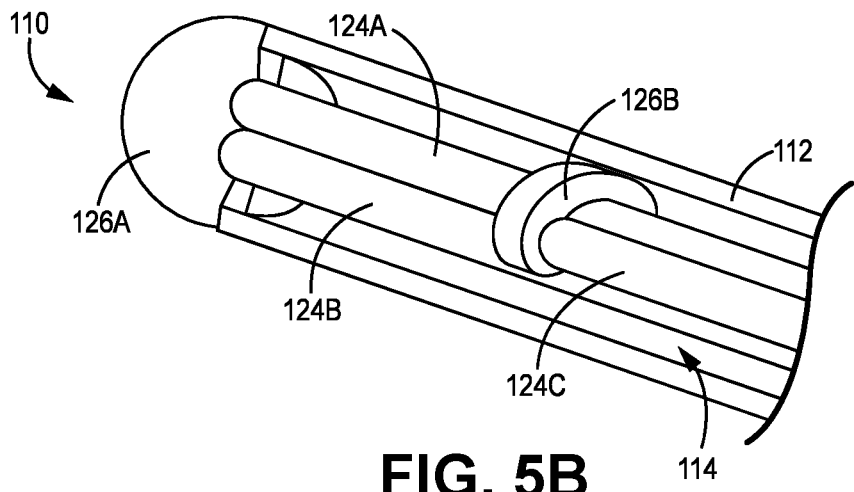
FIG. 5B is an enlarged cross-sectional perspective view of the distal end of the temperature sensing device of FIG. 5A, according to one embodiment.
Figure 5C:
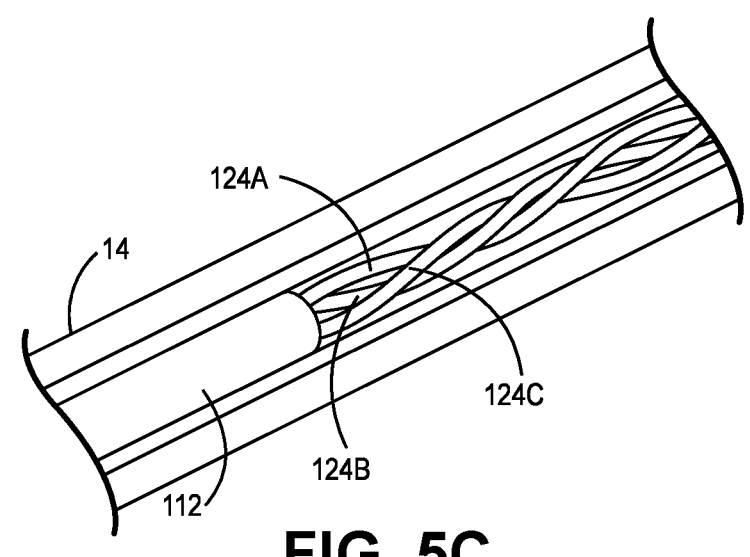
FIG. 5C is an enlarged cross-sectional perspective view of the temperature sensing device of FIG. 5A disposed within an electrode device, according to one embodiment.

Alternatively, the temperature sensing device 110 as shown in FIGS. 5A-5C has two temperature sensors 126A, 126B. Except as expressly described herein, the various components and features of the device 110 as shown in FIGS. 5A-5C are the same or substantially similar to those of the device 110 as shown in FIGS. 4A-4C and discussed in detail above. In this alternative embodiment of FIGS. 5A-5C, the temperature sensing apparatus 122 has an elongate body 124 made up of three elongate wires 124A, 124B, 124C and two temperature sensors 126A, 126B disposed along the length of the body 124. As best shown in FIGS. 5A and 5B, the first temperature sensor 126A is a thermocouple 126A formed at the distal end of the two wires 124A, 124B, while the second temperature sensor 126B is a thermocouple 126B formed along the length of wire 124A and at the distal end of wire 124C. Alternatively, the temperature sensors 126A-B can be any known form or type of temperature sensors 126A-B.

Figure 6A:
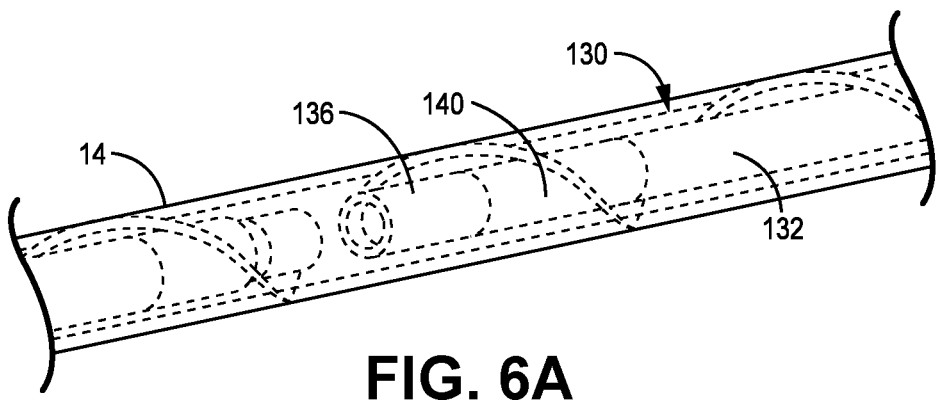
FIG. 6A is a perspective view of an electrode device with a temperature sensing device disposed therein, according to another embodiment.
Figure 6B:
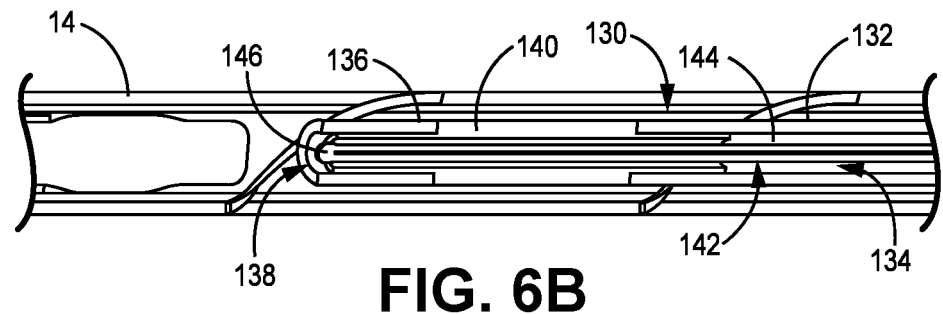
FIG. 6B is an enlarged cross-sectional perspective view of the electrode device with the temperature sensing device disposed therein of FIG. 6A, according to one embodiment.
Figure 6C:
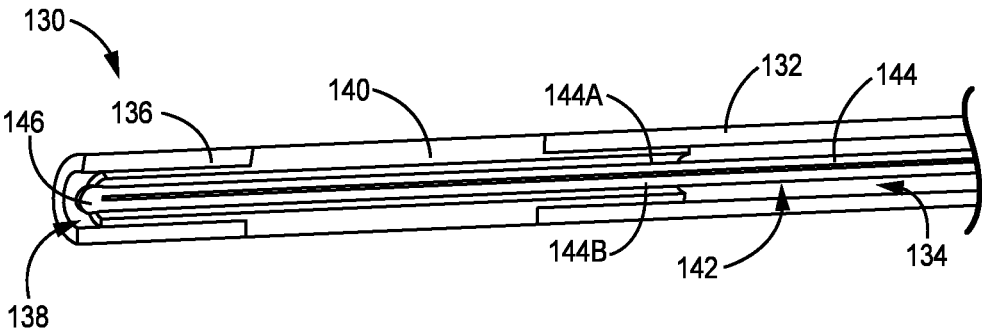
FIG. 6C is an enlarged cross-sectional perspective view of the distal end of the temperature sensing device of FIG. 6A, according to one embodiment.

According to another embodiment, a temperature sensing device implementation 130 is depicted in FIGS. 6A-6C. More specifically, FIGS. 6A and 6B show the device 130 disposed within an ablation probe 14, while FIG. 6C depicts the distal end of the device 130. The device 130 has an elongate body 132 that is a hypotube 132 with a lumen 134 defined therein, a distal body 136 with a lumen 138 defined therein, an adapter 140 coupling the elongate body 132 and the distal body 136, and a temperature sensing apparatus 142 disposed within the lumens 114, 138 and the adapter 140. The adapter 140 is included in the device 130 to connect the hypotube 132 to the distal body 136 that can be, in certain embodiments, a machined tip 136.

The temperature sensing apparatus 142 has an elongate body 144 and a temperature sensor 146 disposed at the distal end. In this specific embodiment, the temperature sensing apparatus body 144 is two elongate wires 144A, 144B and the temperature sensor 146 is a thermocouple 146 formed at the distal end of the two wires 144A, 144B. Alternatively, the temperature sensor 146 can be any known form or type of temperature sensor 146.

In accordance with one embodiment, the elongate body 132 and distal body 136 of the temperature sensing device 130 are made of stainless steel, aluminum, platinum, nickel, or any other known material having substantially similar mechanical properties. As such, the elongate body 132 and distal body 136 are less flexible (or more rigid) than the elongate bodies 52, 72, 92 discussed in detail above. The adapter 140, in some aspects, can be made of stainless steel, titanium, or any other known material having similar properties. According to some embodiments, the wires 144A,

144B and sensor 146 can be made of copper, nickel, constantan, iron, chromium, platinum, iridium, alloys thereof, any other similar material, or any other material having substantially similar electrical conduction properties. The temperature sensing apparatus 142, in accordance with certain aspects, can be positioned within the lumen 134 with an epoxy or other known filling material with similar properties such that the temperature sensing apparatus 142 is positioned as desired.

The elongate body 132 and the distal body 136 can have a diameter ranging from about 100 µm to about 2 mm, while the lumens 134, 18 can have an inner diameter ranging from about 50 µm to about 1.95 mm. Further, the distal body 136 can have a length ranging from about 75 µm to about 5 mm. The adapter 140 can have a diameter ranging from about 50 µm to about 2 mm and a length ranging from about 0.5 mm to about 10 mm. In addition, the device 110 can have a length ranging from about 10 cm to about 1 m.

Figures 7A, 7B, 7C:
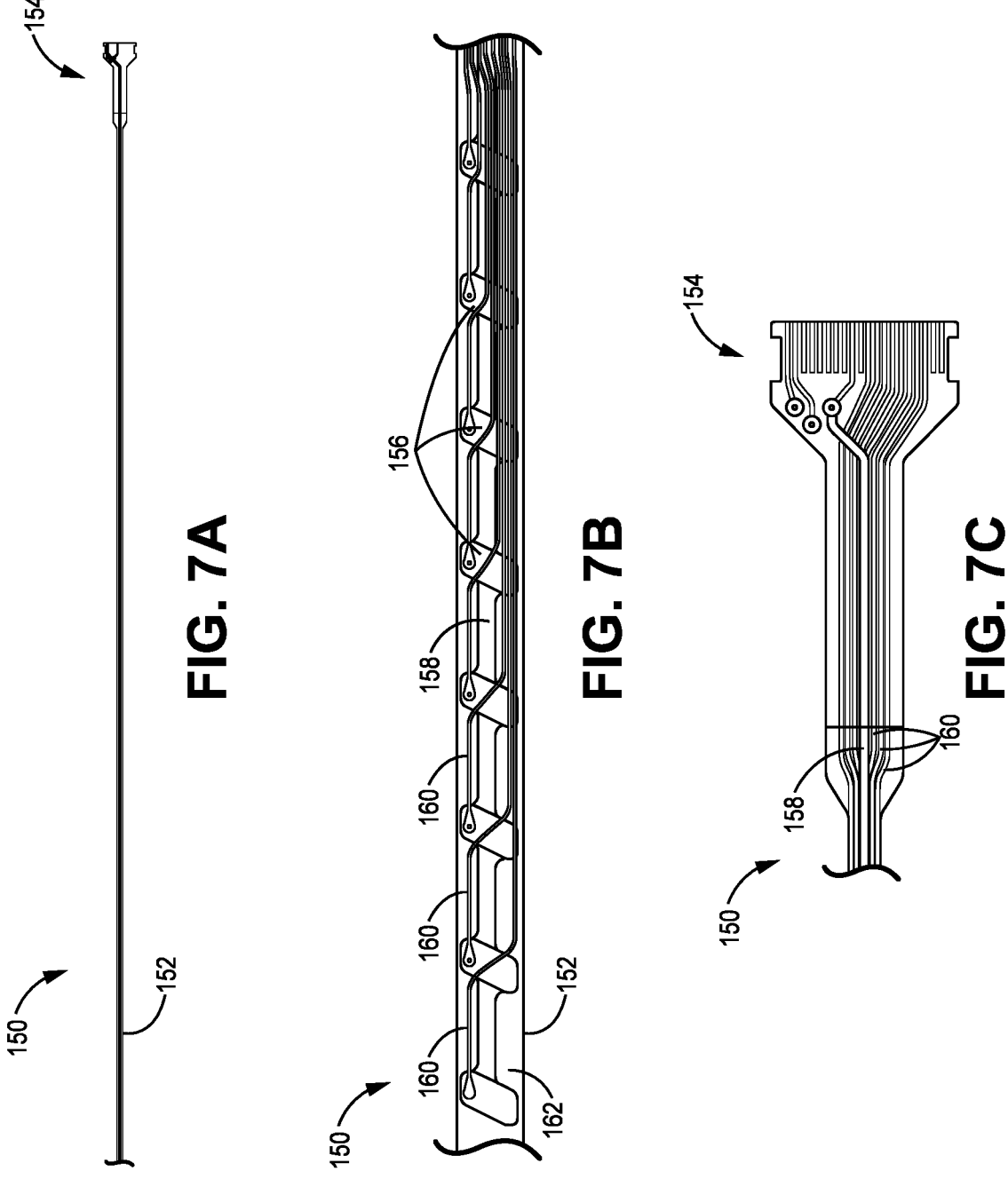
FIG. 7A is a top view of a temperature sensing device, according to another embodiment.
FIG. 7B is an enlarged top view of a portion of the temperature sensing device of FIG. 7A, according to one embodiment.
FIG. 7C is an enlarged top view of a proximal portion of the temperature sensing device of FIG. 7A, according to one embodiment.
Figures 7D, 7E:
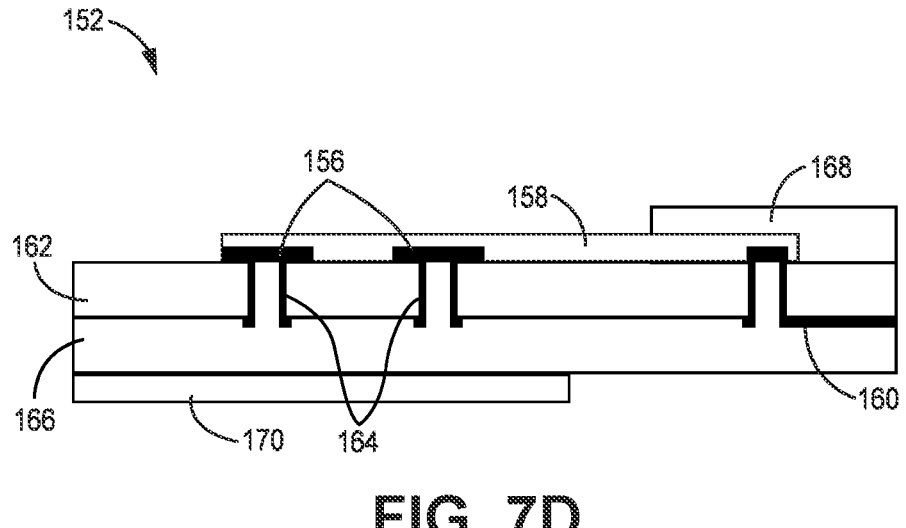
FIG. 7D is a cross-sectional side view of a portion of the temperature sensing device of FIG. 7A, according to one embodiment.
FIG. 7E is an exploded cross-sectional side view of a portion of the temperature sensing device of FIG. 7A, according to one embodiment.

In accordance with various implementations, the temperature sensing device 150 can be a thin film body (or "band," "strip," or "ribbon") 152 as depicted in FIGS. 7A-7E that is wrapped around an elongate core body (not shown), which is an elongate rod or tube. In these embodiments, in contrast to the various single-sensor devices discussed above with respect to FIGS. 2A-6C, the device 150 has multiple temperature sensors. Thus, in use, the device 150 can be positioned within an ablation probe (as discussed above) such that each sensor is disposed adjacent to a different contact. FIG. 7A depicts a top view of the device 150, with the elongate thin film ribbon 152 and a proximal connector 154. FIG. 7B depicts an enlarged cross-sectional top view of a portion of the length of the elongate ribbon 152, while FIG. 7C depicts an enlarged cross-sectional top view of the proximal connector 154. FIG. 7D depicts a cross-sectional side view of the ribbon 152, while FIG. 7E depicts an exploded view of FIG. 7D.

As best shown in FIGS. 7B and 7D, the elongate ribbon 152 has multiple temperature sensors 156 disposed on the ribbon 152. More specifically, in this specific embodiment, the temperature sensors 156 are thermocouple junctions 156 of two different metals. Thus, each sensor 156 is electrically coupled to both (1) a single common elongate conductor (or "common trace") 158, and (2) a separate elongate conductor (or "separate trace") 160 that is made of a different metal in comparison to the common trace 158. In other words, there is a single common trace 158 that extends along the length of the ribbon 152 to the proximal connector 154 and is electrically coupled to every sensor 156, while there are also multiple separate traces 160, with each separate trace 160 being coupled to a different sensor 156 and extending to the proximal connector 154. In one embodiment, the common trace 158 is constantan, while the separate traces 160 are copper. Alternatively, the common trace 158 and the separate traces 160 can be copper, nickel, constantan, iron, chromium, platinum, rhodium, iridium, and/or their alloys.

As best shown in FIGS. 7D and 7E, each sensor 156 and the common trace 158 are disposed on the top surface of a first or base dielectric layer 162. Further, each sensor 156 is electrically coupled to a via 164 that extends through the layer 162 (from the top surface to the bottom surface of the layer 162 as shown). In addition, each via 164 is electrically coupled to one of the separate traces 160 on the bottom surface of the layer 162. Thus, each via 164 electrically couples one sensor 156 to a separate trace 160 through the base layer 162 as shown.

The ribbon 152 also has a second dielectric layer 166 disposed on or attached to the bottom side of the first layer 162 as shown, thereby providing insulation to the separate traces 160 and the bottom portions of the vias 164. In addition, according to certain alternative embodiments, the ribbon 152 can also have a third or top dielectric layer 168 to provide insulation to the common trace 158. In such embodiments, the top layer 168 is disposed solely along a proximal length of the ribbon 152. Further, in certain optional implementations, an adhesive layer 170 can be provided on the bottom surface of the second layer 166 as shown. Such a layer 170 can be used to adhere the ribbon 152 to the target core body (not shown).

As shown in FIG. 7B, according to certain optional implementations, the temperature sensors 156 can be disposed on the ribbon 152 at an angle in relation to the longitudinal axis of the ribbon 152. When the ribbon 152 is wrapped around the core body (not shown), the angled positioning of each sensor 156 allows for each sensor 156 to be positioned substantially around the entire circumference of the core body. Further, each sensor 156 is positioned along the length of the ribbon 152 such that when the ribbon 152 is wrapped around the core body, each sensor 156 is disposed adjacent to a contact on the target electrode device when the temperature sensing device is positioned in that electrode device.

Figure 8A:
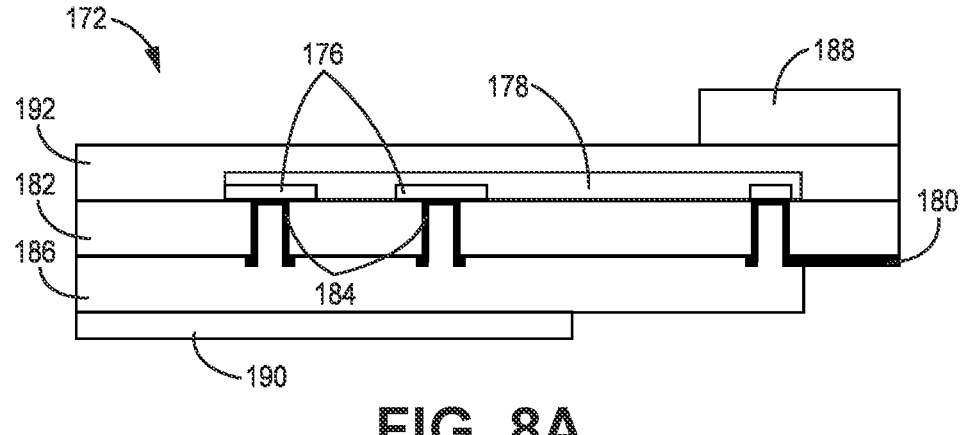
FIG. 8A is a cross-sectional side view of a portion of a temperature sensing device, according to a further embodiment.
Figure 8B:
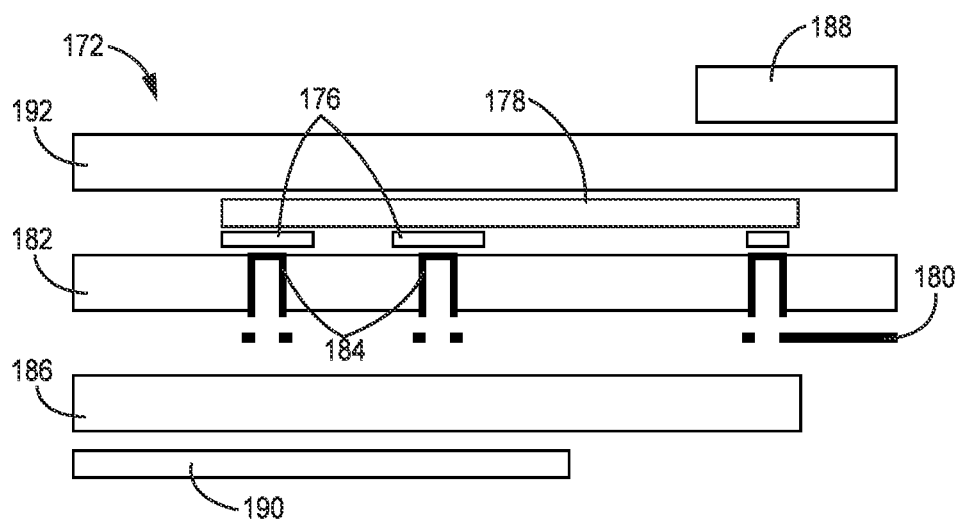
FIG. 8B is an exploded cross-sectional side view of a portion of the temperature sensing device of FIG. 8A, according to one embodiment.

An alternative ribbon 172 configuration is depicted in FIGS. 8A and 8B. As such, the ribbon 172 is substantially similar to the ribbon 152, such that the various components, features, and functionality of the ribbon 172 are number similarly and are substantially similar to the ribbon 152 except as detailed herein. In this particular embodiment, the ribbon 172 has an additional dielectric layer 192 disposed on the top surface of the base layer 182 and the common trace 178 as shown. This additional layer 192 can be used to enhance the mechanical reliability of the device as well as to make the device water proof such that it can accurately measure temperature in moist or wet environments.

In various embodiments, the elongate core body (not shown) is a flexible shaft that can be made of stainless steel, nitinol, tungsten, or other known materials with similar mechanical properties. In certain embodiments, the flexible shaft is an elongate shaft with no lumen defined therethrough. Alternatively, the shaft can have a lumen (not shown) defined therethrough.

Another implementation of a temperature sensing device 200 with a core body 206 and an elongate wire array (or ribbon) 208 is depicted in FIGS. 9A-9F. The device 200 has an elongate body 202 with a probe attachment mechanism 204 disposed at or near a proximal end of the body 202. As best shown in FIGS. 9B-9E, the elongate body 202 of the device 200 has an elongate tube, rod, or core (also referred to as a "shaft") 206 with an elongate wire array 208 wrapped around the core 206 in a helical fashion and a proximal connection mechanism 204 disposed at a proximal end of the shaft 206.

Figures 9A, 9B, 9C:
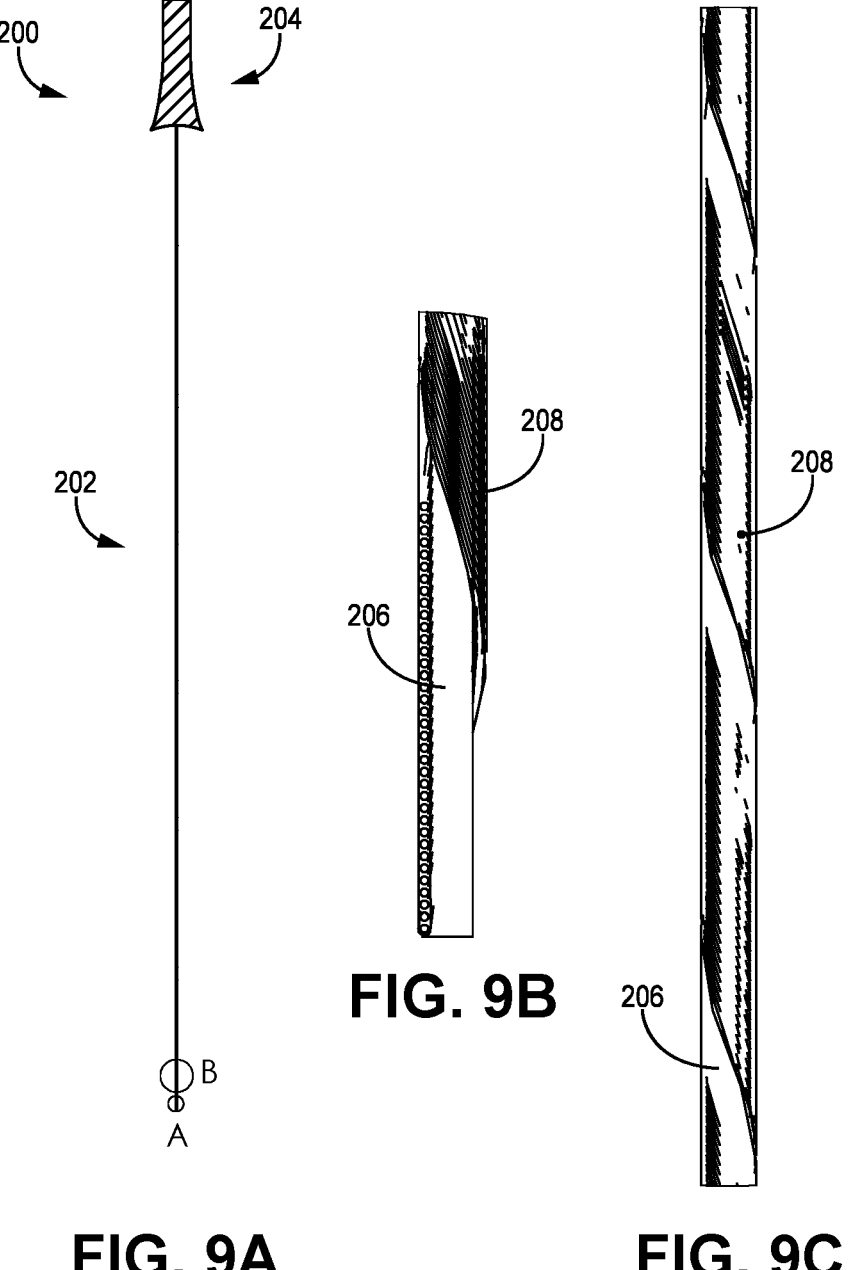
FIG. 9A is a top view of a temperature sensing device, according to yet another embodiment.
FIG. 9B is an enlarged cross-sectional view of a portion of the temperature sensing device of FIG. 9A, according to one embodiment.
FIG. 9C is an enlarged top view of a portion of the temperature sensing device of FIG. 9A, according to one embodiment.
Figures 9D, 9E, 9F:
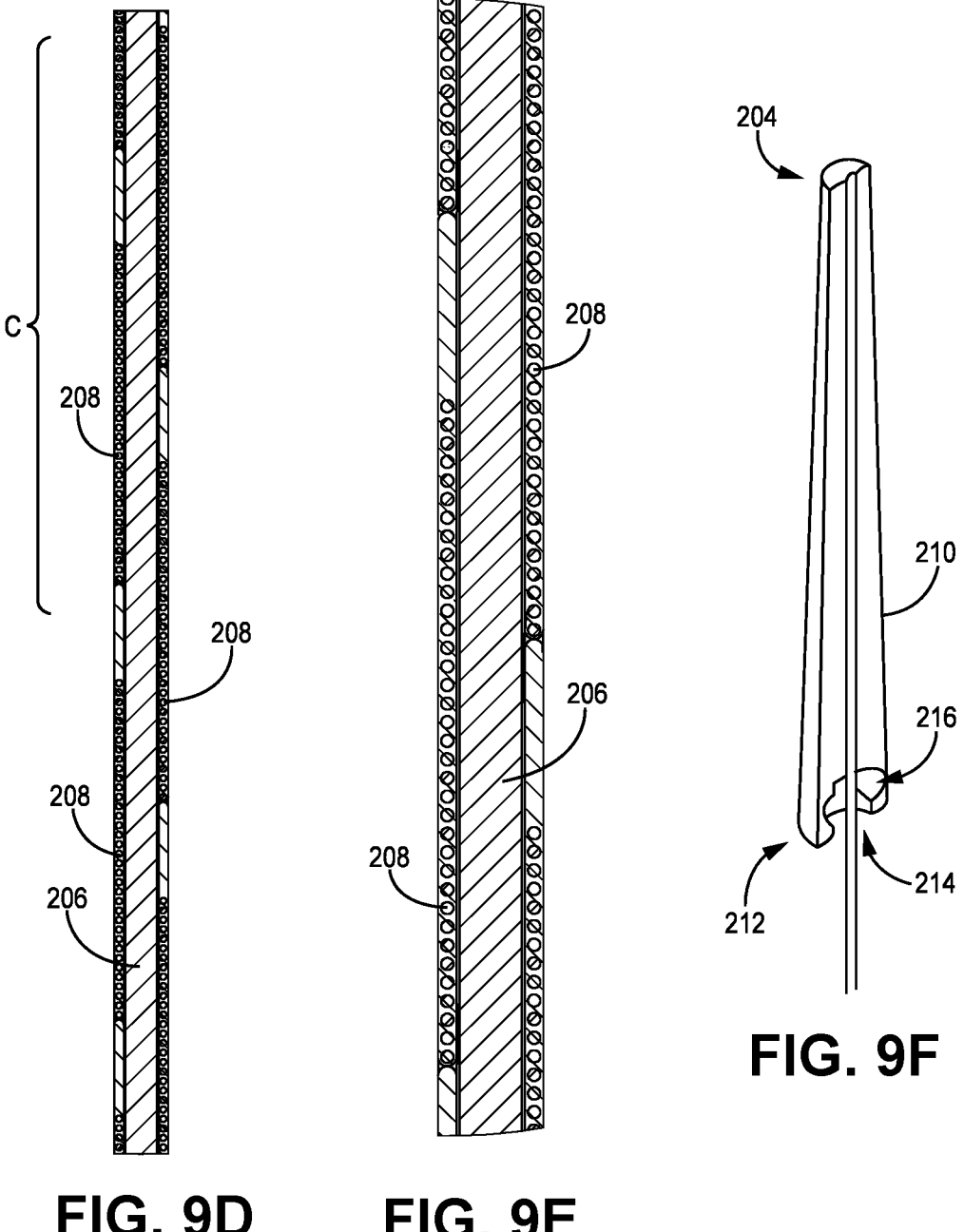
FIG. 9D is a cross-sectional side view of a portion of the temperature sensing device of FIG. 9A, according to one embodiment.
FIG. 9E is an enlarged cross-sectional side view of a portion of the temperature sensing device of FIG. 9A, according to one embodiment.
FIG. 9F is a cross-sectional perspective view of the proximal connection mechanism of the temperature sensing device of FIG. 9A, according to one embodiment.

In one embodiment, the elongate core 206 of the body 202 is a flexible shaft 206 that can be made of stainless steel, nitinol, tungsten, or other known materials with similar mechanical properties. In certain embodiments, the flexible shaft 206 is an elongate shaft 206 with no lumen defined therethrough, as best shown in FIGS. 9D and 9E. Alternatively, the shaft 206 can have a lumen (not shown) defined therethrough.

According to certain implementations as best shown in FIG. 9F, the proximal connection mechanism 204 has an elongate body 210 with a mating feature 212 at the distal end of the body 210 to couple with the ablation probe (such as probe 14). In one embodiment, the mating feature 212 is an opening 214 defined at the distal end of the body 210 with a cavity 216 defined therein. The opening 214 has a smaller diameter than the cavity 216 such that a lip (not shown) at the proximal end of the probe 14 can be inserted into and thereby retained within the cavity 216 by the opening 214. Alternatively, any known mating feature 212 for coupling the temperature sensing device 16 to the probe 14 can be used.

Figures 10A, 10B, 10C, 10D:
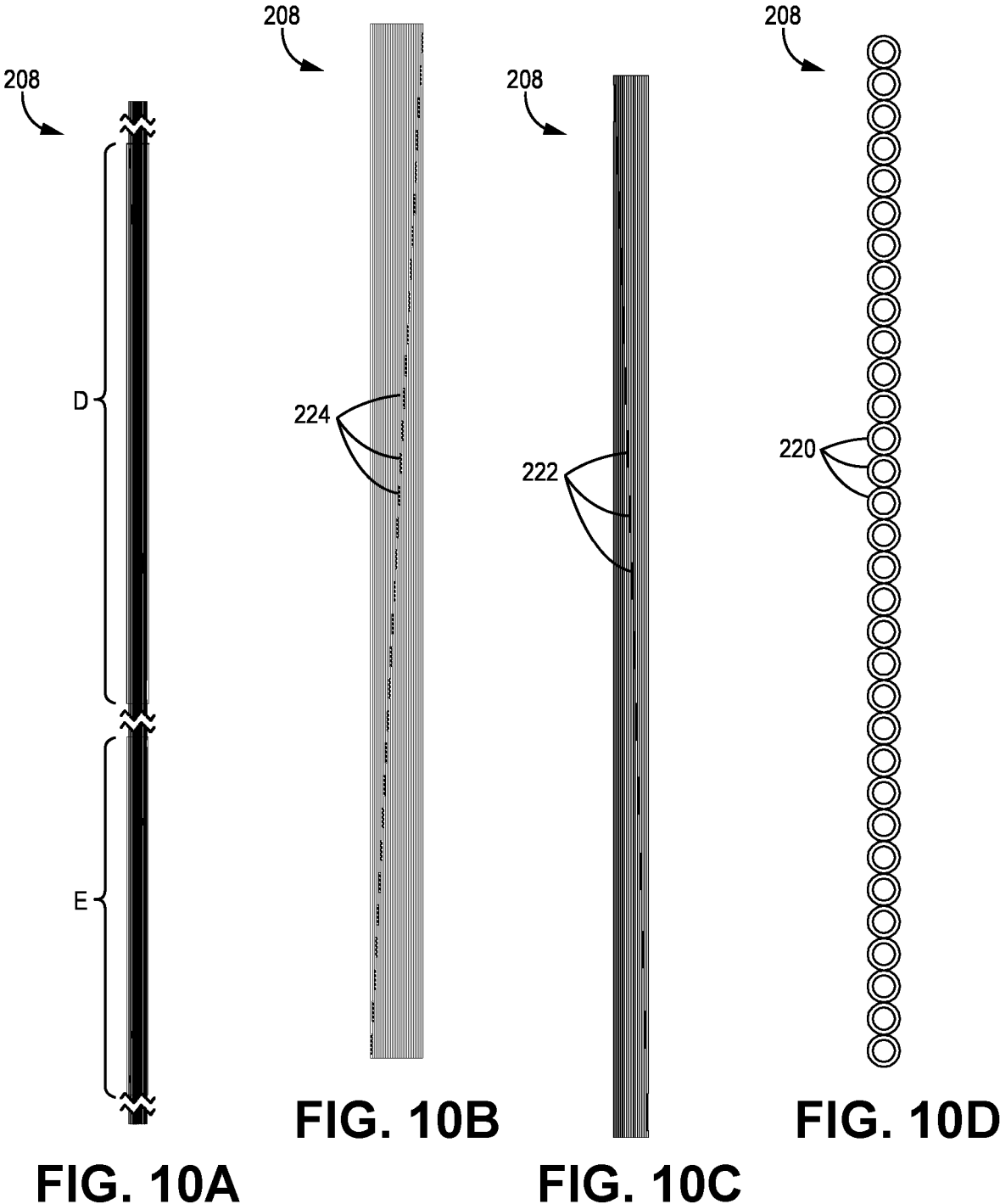
FIG. 10A is a top view of the flexible ribbon of the temperature sensing device of FIG. 9A, according to one embodiment.
FIG. 10B is an enlarged top view of a portion of the flexible ribbon of FIG. 10A, according to one embodiment.
FIG. 10C is an enlarged top view of a different portion of the flexible ribbon of FIG. 10A, according to one embodiment.
FIG. 10D is an enlarged cross-sectional view of the flexible ribbon of FIG. 10A, according to one embodiment.

As shown in FIGS. 10A-10D, according to one embodiment, the elongate wire array 208 disposed around the shaft 206 is a flexible ribbon 208 made up of multiple wires 220 (as best shown in FIG. 10D). In one specific implementation, the ribbon 208 has 32 wires 220. Alternatively, the number of wires can vary from two wires to as many wires as the outer diameter of the core 206 can accommodate as the array 208 is wrapped around it. FIGS. 10A-10C depict various top views of the ribbon 208, while FIG. 10D depicts a cross-sectional view of the ribbon 208 showing all of the thirty-two wires 220 in this exemplary embodiment.

The ribbon 208 has multiple temperature sensors 222 disposed along the length thereof. More specifically, as best shown in FIG. 10C, each of the temperature sensors 222 is disposed at a predetermined location along the length of the ribbon 208 such that each sensor 222 in the array 208 is disposed at a different longitudinal position along the length thereof. Thus, each of the temperature sensors 222 occupies a unique position along the length of the ribbon 208 as shown in FIG. 10C such that each sensor 222 is disposed adjacent to a contact (not shown) on the probe 14 when the ribbon 208 is disposed around the shaft 206 and the temperature sensing device 16 is disposed within the probe 14 as described in additional detail herein.

In certain implementations, the temperature sensors 222 are thermocouples 222, with two adjacent wires 220 coupled together to form each thermocouple 222. As is necessary for the operation of a thermocouple 222, each of the two adjacent, paired wires 220 are made of different metals such that the thermocouple 222 of that pair can operate to detect temperature. Thus, in the embodiments in which the array 208 has thirty-two wires 220, sixteen pairs of the wires 220 are coupled together to form sixteen thermocouples 222. Alternatively, the temperatures sensors 222 can be thermistors. In a further alternative, the temperature sensors 222 can be any known temperature sensors for use in a similar medical device.

The temperature sensors 222 in some embodiments are positioned along a distal portion of the ribbon 208 as shown in FIGS. 10A and 10C. FIG. 10C is an enlarged view depicting the distal length of the ribbon 208 identified with reference letter D in FIG. 10A.

In addition, according to certain implementations, the ribbon 208 has multiple solder joints 224 disposed along a length thereof. More specifically, as best shown in FIG. 10B, each of the solder joints 224 is disposed at a predetermined location along the length of the ribbon such that each joint 224 in the array 208 is disposed at a different longitudinal position length thereof. Thus, much like the temperature sensors 222, each of the solder joints 224 occupies a unique position along the length of the ribbon 208 as shown in FIG. 10B. The purpose of the solder joints 224 is to aid in the coupling of the ribbon cable 208 to a flexible circuit board or a printed circuit board that is coupled to the connector box 20. Each solder joint 224 forms an electrical connection between the terminal of the thermocouple junctions 222 and the rest of the system. In accordance with some embodiments, the arrangement of the solder joints 224 as described and depicted herein (that is, the positioning of each joint 224 so that it is not axially adjacent to the other joints 224) decreases the possibility of electrical shorting during assembly.

In certain implementations, each wire 220 has a solder joint 224. In the exemplary embodiments in which the array 208 has thirty-two wires 220, the array has thirty-two solder joints 224. The joints 224 according to some embodiments are positioned along a proximal portion of the ribbon 208 as shown in FIGS. 10A and 10B. FIG. 10B is an enlarged view depicting the proximal length of the ribbon 208 identified with reference letter E in FIG. 10A.

Figure 11A:
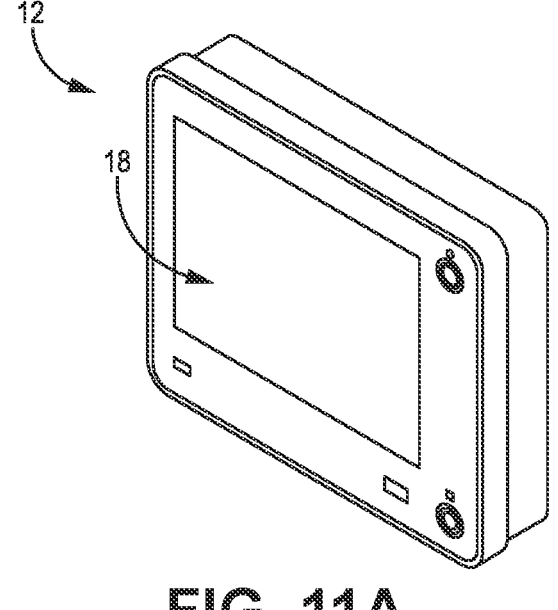
FIG. 11A is a perspective view of a controller, according to one embodiment.
Figure 11B:
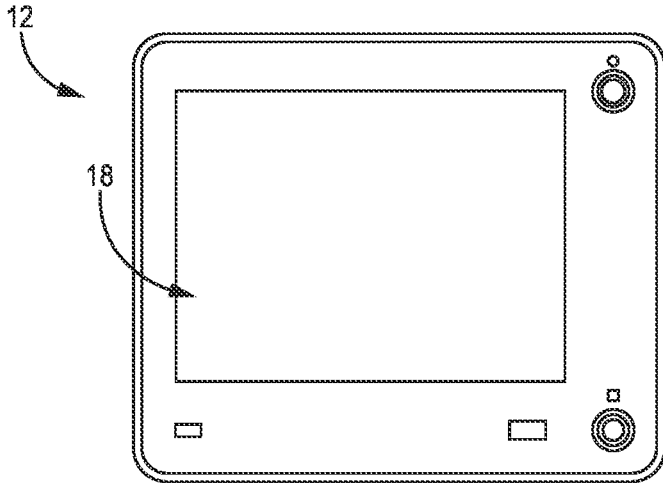
FIG. 11B is a front view of the controller of FIG. 11A, according to one embodiment.

FIGS. 11A and 11B depict the controller 12, according to one embodiment. In this implementation, the controller 12 has an interface 18 that can provide information about the system 10 and further can be an interactive touchscreen 18 such that a user can provide inputs to the system 10 via the touchscreen 18. Various information can be displayed on the interface 18 as shown in FIG. 1A, for example. Alternatively, the controller 12 can have input buttons or any other mechanism or feature that allows for providing inputs to the system 10.

Figure 12:
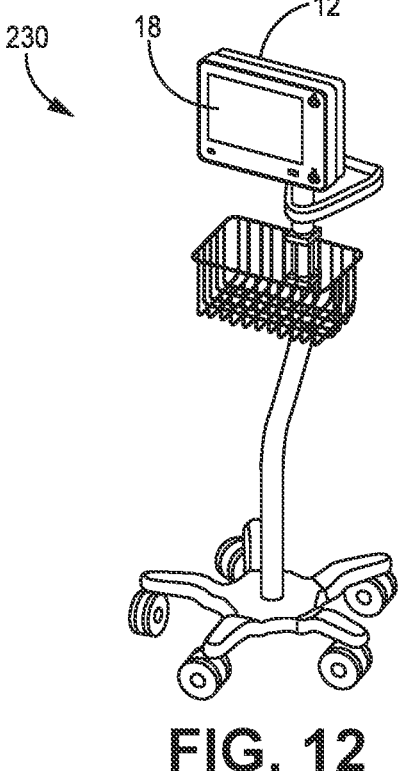
FIG. 12 is a perspective view of a controller disposed on a wheeled cart, according to one embodiment.

In certain implementations, the controller 12 can be disposed on a wheeled cart 230 as shown in FIG. 12. Alternatively, the controller 12 can be on any type of cart or apparatus, or, in a further alternative, can be a standalone unit.

Figure 13:
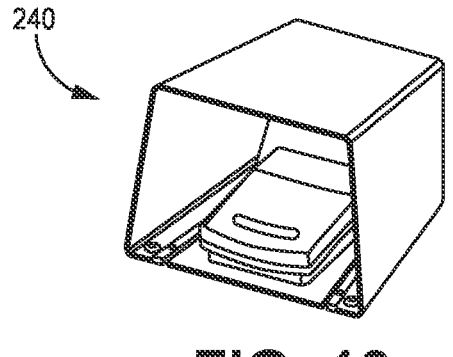
FIG. 13 is a perspective view of a foot pedal that can be used with the controller, according to one embodiment.

In further embodiments, such as the exemplary embodiment in FIG. 13, the system 10 can also have a foot pedal 240 that can be used in conjunction with the controller 12 to control the system 10. More specifically, in some exemplary implementations, the pedal 240 is used to actuate (and terminate) the delivery of the RF energy via the probe 14.

Figure 14A:
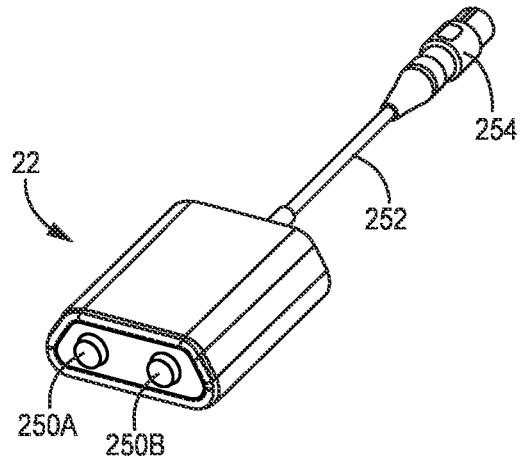
FIG. 14A is a perspective view of a controller interface box and connector cable, according to one embodiment.
Figure 14B:
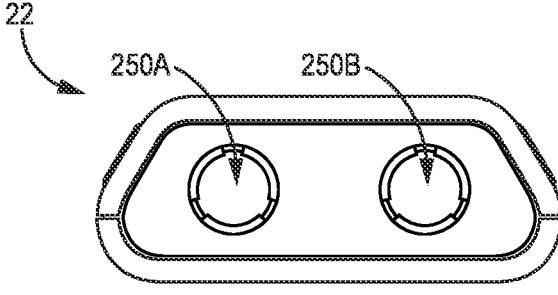
FIG. 14B is an end view of the controller interface box of FIG. 14A, according to one embodiment.
Figure 15A:
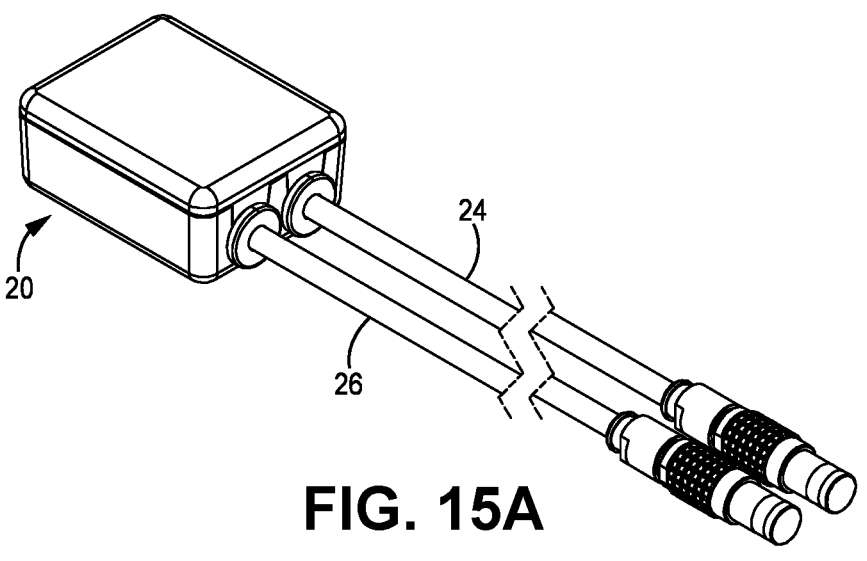
FIG. 15A is a perspective view of a connector box with two cables extending therefrom, according to one embodiment.
Figure 15B:
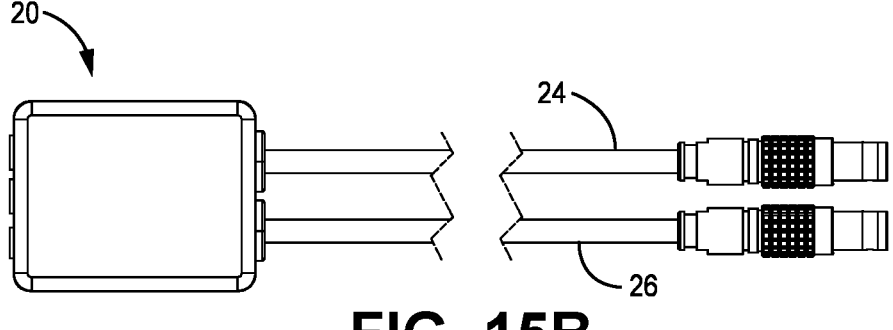
FIG. 15B is a top view of the connector box and cables of FIG. 15A, according to one embodiment.
Figure 15C:
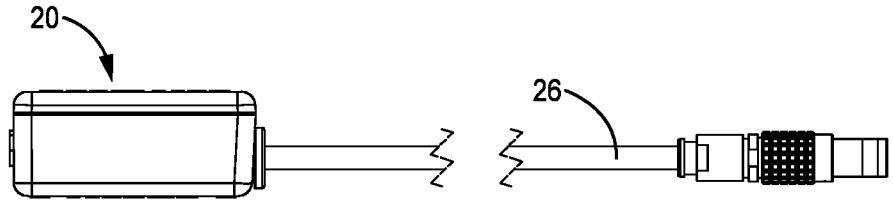
FIG. 15C is a side view of the connector box and cables of FIG. 15A, according to one embodiment.
Figure 15D:
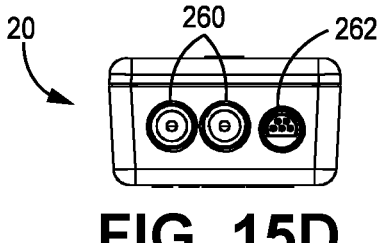
FIG. 15D is an end view of the connector box of FIG. 15A, according to one embodiment.

One embodiment of the controller interface box 22 is depicted in FIGS. 14A-14B. As shown, the box 22 has two input ports 250A, 250B configured to receive the cables 24, 26, as best shown in FIGS. 14B and 1A. Further, the box 22 is coupled to a single connector cable 252 that is coupled to the controller (such as controller 12 discussed above) via a connector 254. In accordance with certain implementations, the controller interface box 22 can operate to combine all electrical wires and other elongate components from the two cables 24, 26 into the single connector cable 252 as shown. In certain embodiments, this interface box 22 and conversion from two cables 24, 26 to one cable 252 allows the coupling of the two devices 14, 16 and associated components to commercially available controllers (such as controller 12) that has a single port for receiving a single cable (such as cable 252). Alternatively, for any controllers 12 having two ports, no controller interface box is needed.

One exemplary implementation of a connector box 20 that couples to the probe 14 and temperature sensing device 16 and further couples to the two cables 24, 26 is shown in FIGS. 15A-15D. In this implementation, the connector box 20 is configured to be used with temperature sensing device embodiments having a single temperature sensor (such as any of devices 50, 70, 90, 110, 130). As shown, the connector box has two input ports 260 to receive the connectors from the ablation probe (such as probe 14). Further, the connector box also has an input port 262 to receive the connector from the temperature sensing device (such as device 16). The connector box 20 operates to receive the inputs from the ablation probe (such as probe 14) and the temperature sensing device (such as device 16) and convert those inputs into two separate outputs associated with the contacts of the ablation probe.

Figure 16:
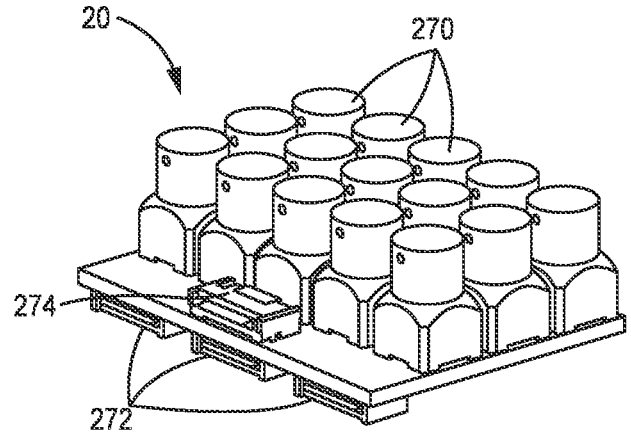
FIG. 16 is a perspective view of a connector box, according to another embodiment.

Alternatively, a connector box 20 as shown in FIG. 16 is used with temperature sensing device embodiments having multiple temperature sensors (such as either of devices 150, 200 as discussed in detail above). The box 20 has multiple output connections (or "ports") 270, each of which can receive and couple to either of the cables 24, 26 discussed above. In addition, the box 20 has at least one temperature input connection (or "port") 272 to receive the proximal connector of any multi-sensor temperature sensing device embodiment herein (including devices 150, 200, for example). More specifically, the exemplary box 20 embodiment as shown in FIG. 16 has three temperature input ports 272, each of which is configured to receive the proximal connector of any multi-sensor temperature sensing device embodiment. Alternatively, the connector box 20 can have one, two, three, four, or any number of temperature input ports 272. Further, the connector box 20 has a probe input connection (or "port") 274 to receive the proximal connector of any probe device used within any system embodiment disclosed or contemplated herein. Hence, the connector box 20 operates to receive the inputs from any ablation probe (including probe 14) (via the probe input port 274) and any temperature sensing device (including device 16) (via one of the temperature input ports 272) and convert those inputs to two separate output ports 270 associated with the contacts of the probe device used.

Figure 17:
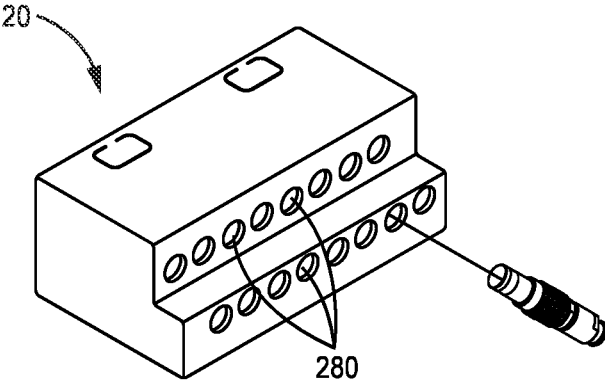
FIG. 17 is a perspective view of another connector box, according to a further embodiment.

A further alternative connector box 20 for use with temperature sensing device embodiments having multiple temperature sensors (such as device 150, 200) is depicted in FIG. 17. In this implementation, the connector box 20 has multiple output connections (or "ports") 280, each of which can receive and couple to either of the cables 24, 26 discussed above. Further, the connector box 20 couples to any multi-sensor temperature sensing device embodiment and probe device via at least two input ports configured to receive the proximal connectors of the two devices in a fashion similar to that described above with respect to the connector box embodiment depicted in FIG. 16. The two ports are not visible in FIG. 17 because they are disposed on the side of the box 20 opposite the multiple ports 120. As with the box 20 embodiment above, this box 20 can have two or more input ports for the temperature sensing device. The connector box 20 operates to receive the inputs from the ablation probe and temperature sensing device and convert those inputs to two separate outputs 280 associated with the contacts of the probe device used.

Returning now to the controller 12 as shown in FIGS. 1A, 1B, 11A, 11B, and 12, various implementations of the controller 12 can be used to operate any of the ablation system 10 embodiments disclosed or contemplated herein. More specifically, the controller 12 can operate the ablation probe (such as probe 14) based at least in part on the temperature information collected by the temperature sensing device (such as device 16 or any other embodiment disclosed or contemplated herein). In use, when the temperature sensing device is disposed within the probe and the probe is being used to ablate the target tissue, a temperature sensors can be used to detect the temperature of a specific contact in the ablation probe. That temperature information is transmitted to the controller such that the controller can use the temperature information to adjust the energy being supplied to the specific contact (not shown) in question. In other words, the ablation systems herein are temperature-modulated or temperature-controlled ablation systems as a result of the controller 12 operating in conjunction with the temperature sensing device and the ablation probe as described herein.

In one embodiment, the controller 12 can have operational software or can have operational algorithms programmed into the hardware therein to operate the ablation system 10. For example, in certain implementations, the controller 12 can have software and/or an algorithm that utilizes impedance control and a maximum power. Further, the controller 12 can also have software and/or an algorithm that uses temperature sensing to control the ablation as performed by the ablation probe. That is, the algorithm is configured to utilize the temperature information from the temperature sensing device to control the operation of the ablation probe. In addition, the controller 12 can have software and/or an algorithm that controls the temperature sensing device to measure temperature after ablation energy is delivered by the ablation probe and then delivers additional energy to the probe. The controller 12 can also be configured to deliver ablation using constant RF or, alternatively, pulsed RF. Further, the controller 12 can be configured to control which of the one or more contacts (not shown) of the probe is actuated to ablate tissue. In one embodiment, a user can depress a button or otherwise use the touchscreen 18 to select the specific contact or contacts to actuate for ablation.

Figure 18A:
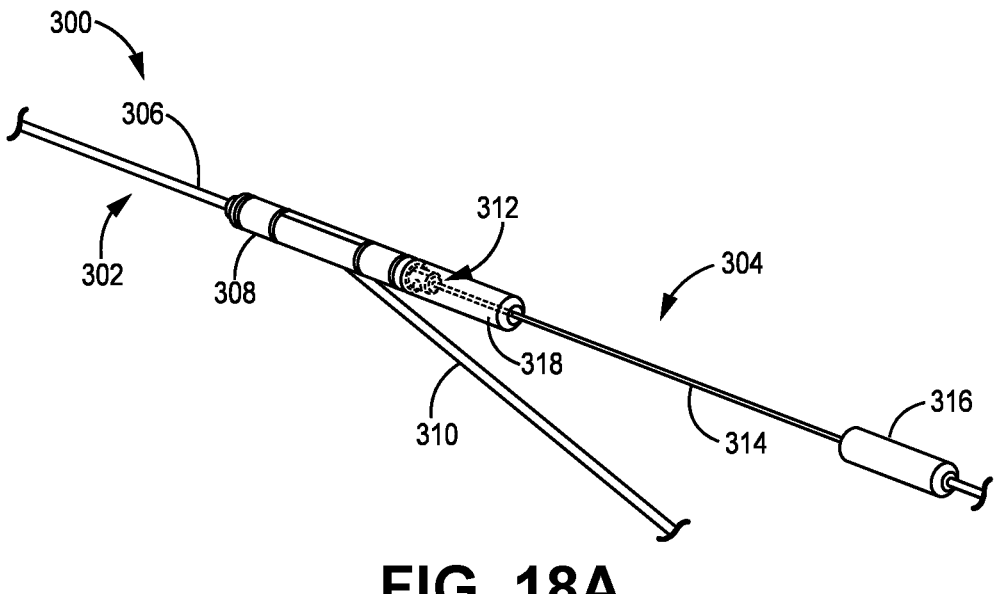
FIG. 18A is a perspective view of an electrode device and a temperature sensing device with a spacing device coupled thereto, according to another embodiment.
Figure 18B:
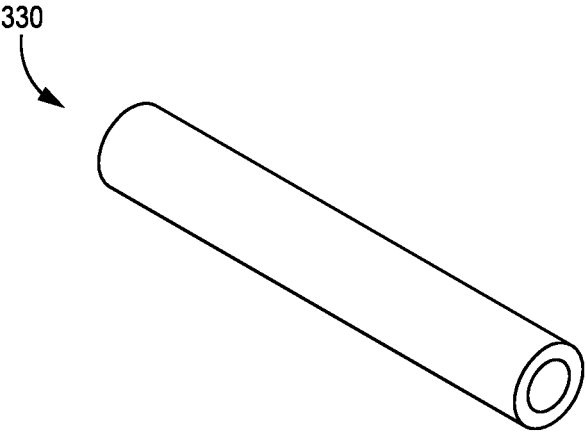
FIG. 18B is a perspective view of a spacing device, according to one embodiment.
Figure 18C:
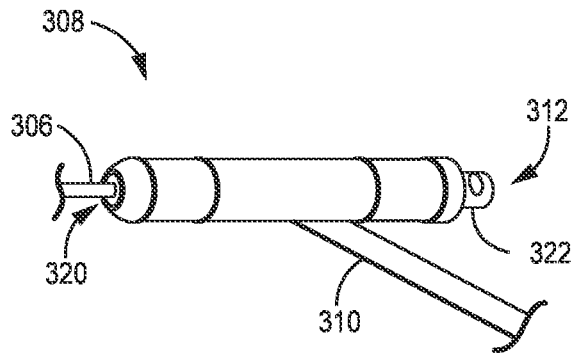
FIG. 18C is a perspective view of a proximal support structure for an electrode device, according to another embodiment.
Figure 18D:
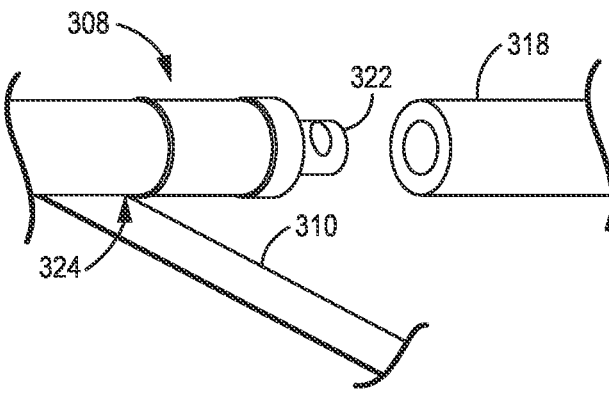
FIG. 18D is an expanded perspective view of the proximal support structure of FIG. 18C, according to one embodiment.

A further embodiment of a system 300 (similar to system 10 above) having an ablation probe 302 and a temperature sensing device 304 is shown in FIGS. 18A and 18B, with the probe 302 having an elongate body 306, a proximal support structure 308, and a tail 310 extending proximally from the support structure 308 as shown. Except as expressly discussed herein, the various structures, components, and features of the system 300—including those not identified or discussed herein—can be substantially similar or identical to the corresponding structures, components, and features of the system 10. As best shown in FIGS. 18A, 18C, and 18D, the structure 308 can have an opening 312 at the proximal end thereof such that the distal end (not shown) of the temperature sensing device 304 is inserted therethrough such that the distal portion of the device 304 is disposed within the probe 302 as shown. The temperature sensing device 304 has an elongate body 314 with a connection (or "probe attachment") mechanism 316 disposed along the length of the body 314 as shown. The connection mechanism 316 is configured to couple to the support structure 308 when the temperature sensing device 304 is inserted into the probe 302, thereby coupling to device 304 to the probe 302 and stopping the distal progress of the device 304 within the probe 302. In addition, as best shown in FIG. 1C, in some embodiments the system 300 can also have a spacing device (or "spacer") 318 coupled at its distal end to the structure 308 of the probe 302 such that the connection mechanism 316 couples to the spacer 318 instead of the strain relief structure 308 as shown.

In certain embodiments, either the spacer 318 or the connection mechanism 316 (or both) can be used to control the exact position of the distal end of the temperature sensing device 304 within the probe 302. For example, according to some aspects, the spacer 318 can be an interchangeable spacer 318 that can be selected from several spacers 318 of different predetermined lengths by the surgeon (or other user) in order to position the distal end of the temperature sensing device 304 in a specific position within the probe 302, thereby ensuring that the temperature sensor (not shown) at or near the distal end of the device 304 is disposed in the desired location in relation to a contact (not shown) of the probe 302. Thus, if the surgeon or user desires to position the distal end of the temperature sensing device 304 at or near the distal end of the probe 302, the surgeon or user selects no spacer or a short spacer 318. On the other hand, the more proximal from the distal end of the probe 302 that the surgeon or user desires to position the distal end of the device 304 (in order to position the temperature sensor adjacent to a specific contact that is more proximal from the distal end of the probe 302), the longer the length of the spacer 318 will be that is selected by the surgeon or user. Further, the various spacers 318 can be provided in predetermined lengths that correspond to the specific locations of the contacts within the probe 302. As such, a user can select a specific spacer 318 of a specific length to be coupled to or positioned adjacent to the strain relief mechanism 308 with the knowledge that the spacer 318 will ensure that the sensor (not shown) is disposed adjacent to the desired contact (not shown) when the temperature sensing device 304 is inserted into the probe 302 such that the connection mechanism 316 is placed into contact with the spacer 318.

In further implementations, the connection mechanism 316 can be adjustable along the length of the temperature sensing device 304 such that the surgeon or other user can position the adjustable connection mechanism 316 at a desired location along the length of the device 304, thereby controlling the position of the temperature sensor (not shown) along the distal length of the device 304 (and thus along the length of the probe 302). In other words, the connection mechanism 316 can be used to position the temperature sensor (not shown) within the probe 302 adjacent to the desired contact (not shown). To position the sensor (not shown) next to a contact that is closer to the proximal end of the probe 302, the connection mechanism 316 is positioned closer to the distal end of the temperature sensing device 304. On the other hand, to position the sensor (not shown) next to a contact that is closer to the distal end of the probe 302, the connection mechanism is positioned closer to the proximal end of the temperature sensing device 304.

An exemplary spacer 330 is depicted in FIG. 18B. In certain embodiments, the spacer 330 can have information on the side of the spacer 330, including, for example, the length of the spacer 330. Such information can be used by the surgeon or other user to decide which spacer 330 amongst several spacers to use, depending on the specific contact within the probe 302 adjacent to which the surgeon/user wants to position the sensor (not shown) of the temperature sensing device 304.

With reference to FIGS. 18A, 18C, and 18D, the support structure 308, in one embodiment, is an elongate structure 308 having a distal opening 320, a proximal opening 312 as discussed above, and a lumen (not shown) defined through the structure 308 such that the lumen is in fluidic communication with the distal and proximal openings 320, 312. In addition, the structure 308 has a hub or protrusion 322 (as best shown in FIGS. 18C-D) extending from the proximal end of the structure (such that the proximal opening 312 is actually defined within the hub 322) that facilitates attachment of other devices or structures (such as, for example, a spacing device) to the support structure 308. The support structure 308 is disposed over the proximal end of the elongate body 306 of the electrode device 302 such that the structure 308 is attached to the body 306. Further, the proximal opening 312 of the structure 308 is in fluidic communication with a proximal opening (not shown) at the proximal end of the body 306, thereby providing access to the lumen (not shown) of the electrode body 306. The structure 308 can also have a side opening 324 (as best shown in FIG. 18D) such that the proximal tail 310 that extends from a proximal portion of the elongate body 306 can extend out of the support structure 308 through the side opening 324.

In certain implementations, the support structure 308 has an outer diameter that is greater than the outer diameter of the elongate body 306 of the electrode device 302 and is made of a polymeric material that is thicker than and at least as rigid as the material of the elongate body 306. As such, the support structure 308 is less flexible than the elongate body 306 and thus provides additional structural support to the proximal end of the electrode device 302, including any delicate components disposed therethrough.

Figure 19:
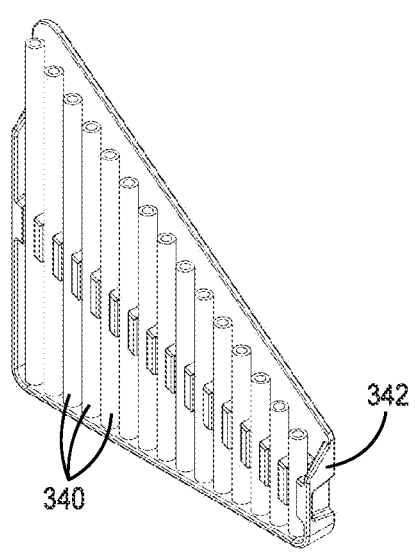
FIG. 19 is a perspective view of a set of spacer devices, according to one embodiment.

Returning to the spacer device, it is noted that a variety of such devices can be provided to ensure that the correct length is available and thus that the temperature sensor(s) of the temperature sensing device can be positioned in the desired position(s) within the electrode device. For example, according to one embodiment, FIG. 19 depicts a set of spacer devices 340 of differing, predetermined lengths disposed in a cassette or other retention or container structure 342 configured to hold the various devices 340. In this embodiment, the surgeon or other user can select any of the various spacers 340 based on the position of the target contact in the probe 302, as discussed in further detail above.

Figure 20:
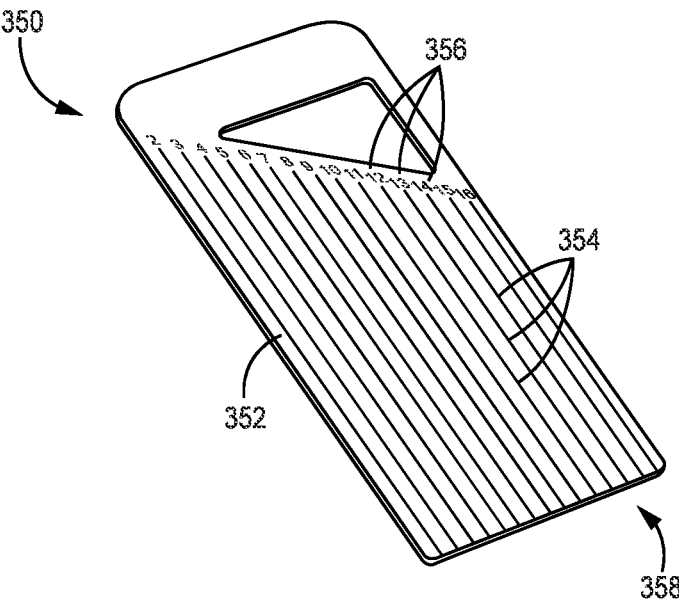
FIG. 20 is a perspective view of a measurement device for use with an adjustable connection mechanism, according to one embodiment.

FIG. 20, in accordance with certain embodiments, depicts a measurement device 350 that can be used with the adjustable connection mechanism 316 to allow the surgeon or other user to position the connection mechanism 316 in the correct location along the length of the temperature sensing device 304 to ensure that the sensor (not shown) is positioned adjacent to the desired contact (not shown). More specifically, in the exemplary implementation as shown, the measurement device 350 is a flat body (or "plate") 352 with specific markings that can be used to position the connection mechanism 316 along the temperature sensing device 304. For example, the device 350 in FIG. 20 has fifteen lines or grooves 354 on the plate 352, wherein each groove 354 represents a desired position of the connection mechanism 316 on the elongate body 314 of the temperature sensing device 304. More specifically, each groove 354 has a length that represents the distance from the distal end of the elongate body 314 of the temperature sensing device 304 to the location that the connection mechanism 316 should be positioned to ensure the sensor (not shown) is disposed adjacent to the target contact (not shown). Further, each groove 354 has a number 356 adjacent to the groove 354 that identifies the corresponding contact (not shown) adjacent to which the sensor (not shown) will be positioned when the connection mechanism 316 is positioned based on the length of the groove 354. In use, the elongate body 314 is positioned adjacent to or in contact with the groove 354 of the desired contact such that the distal end of the body 314 is disposed at the distal end 358 of the plate 352. Once the elongate body 314 is so positioned, the connection mechanism 316 is positioned along the elongate body 314 adjacent to the opposite end of the groove 354 against which the body 314 is positioned. Alternatively, the distal end of the elongate body 314 is disposed at the end of the groove 354 next to the number 356 and the mechanism 316 is positioned along the elongate body 314 adjacent to the distal end 358 of the plate 352. Once the mechanism 316 is positioned as desired and locked in place, the temperature sensing device 304 can be inserted into the probe 302 until the mechanism 316 contacts or is coupled with the strain relief mechanism 308 (or any spacer 318 coupled thereto).

Figure 23:
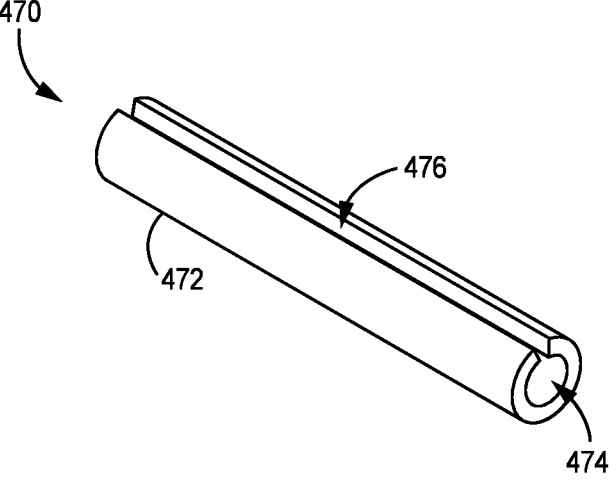
FIG. 23 is a perspective view of another spacing device, according to yet another embodiment.

According to certain further embodiments, any of the spacer embodiments disclosed or contemplated herein can have an elongate opening or slit defined along a length of the spacer such that the spacer can be easily attached to the temperature sensing device by sliding the spacer radially onto the temperature sensing device via the opening. For example, one specific implementation of such a spacing device 470 is depicted in FIG. 23. The device 470 has an elongate body 472 with a lumen 474 defined therethrough. The lumen 474 is configured to receive a temperature sensing device therethrough. In addition, the body 472 also has an opening 476 defined along the length of the body 472 such that the opening 476 provides access to the lumen 474. As such, the spacing device 470 can be added to the temperature sensing device by inserting the temperature sensing device into the lumen 474 via the opening 476 and/or can be removed from the temperature sensing device via the opening 476 as well. Hence, such a spacing device 470 (or set of spacing devices with similar openings) allows for use—including attachment and removal—of the device 470 without having to remove the temperature sensing device from the probe. That is, instead of having to remove the temperature sensing device from the probe in order to add a spacing device or change spacing devices, the spacing device 470 can be added to or removed from the temperature sensing device via the opening 476 while the temperature sensing device is still positioned in the probe as described elsewhere herein.

Figure 21A:
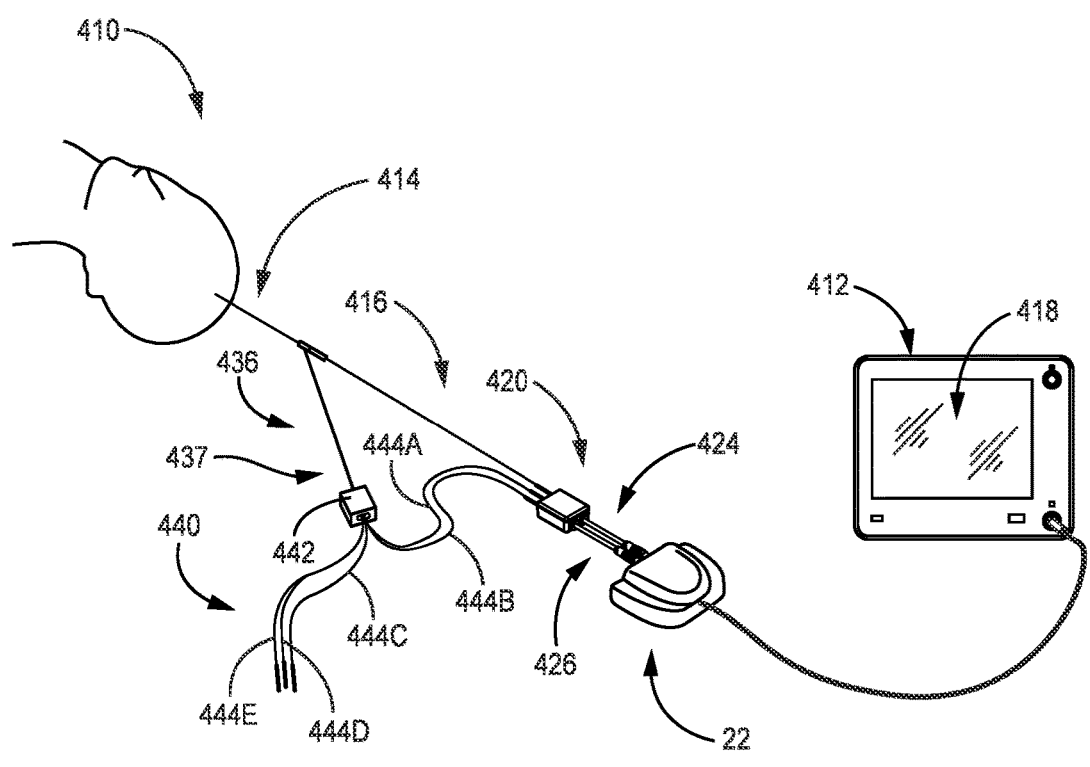
FIG. 21A is a schematic view of another system that includes both an electrode device and a temperature sensing device, according to a further embodiment.
Figure 21B:
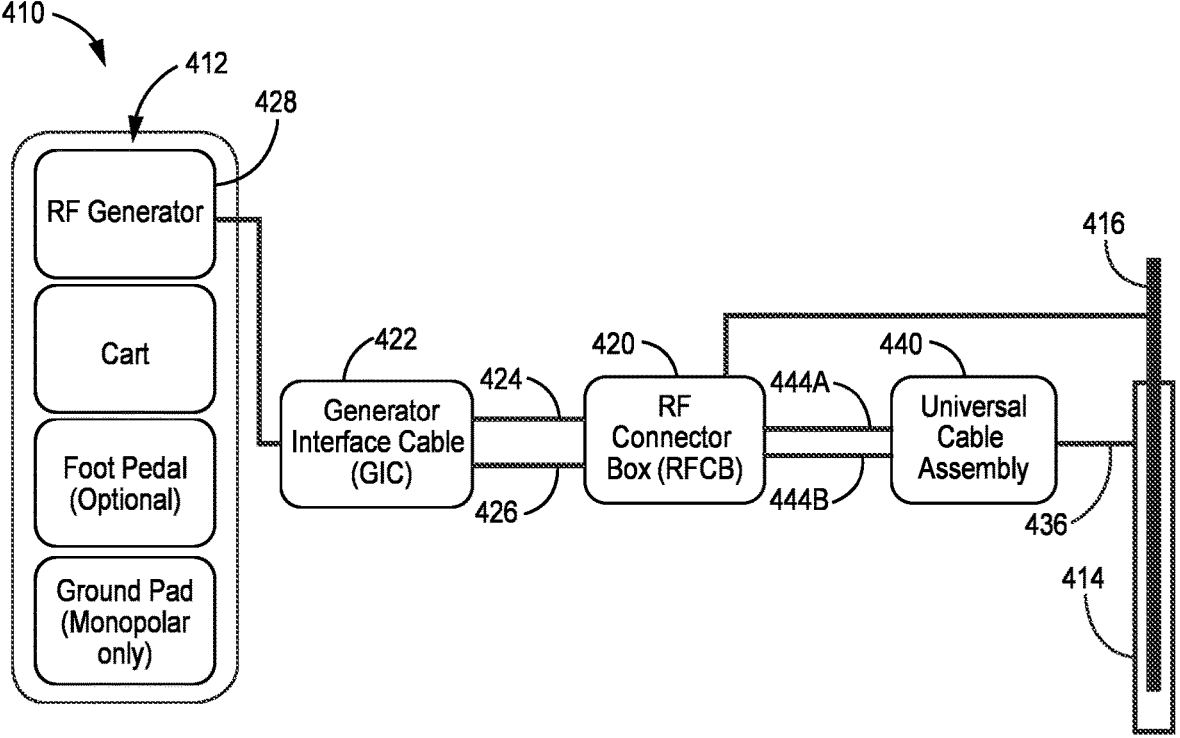
FIG. 21B is a schematic block summary of the system of FIG. 21A, according to one embodiment.

Another implementation of an ablation electrode and temperature sensing device system 410 is depicted in FIGS. 21A and 21B. Except as expressly described herein, the various components and features of the system 410 as shown in FIGS. 21A-21B are the same or substantially similar to those of the device system 10 as shown in FIGS. 1A-1D and discussed in detail above. The system 410 has a controller 412 that is coupled to an ablation probe 414 and a temperature sensing device 416. In certain embodiments, the controller 412 has a radiofrequency generator 428 (as best shown schematically in FIG. 21B) that provides the ablation energy to the ablation probe 414 and has an interactive interface 418 on the controller 412 that is accessible to a user during operation.

As shown in FIGS. 21A and 21B, in certain implementations, the system 410 provides for the controller 412 to be coupled to the ablation probe 414 and temperature sensing device 416 in the following, non-limiting manner. The system 410 can have a connector box 420 to which the probe 414 and device 416 are coupled and further can have a controller interface box 422 coupled to the controller 412, with the connector box 420 and the interface box 422 coupled via first and second cables 424, 426 as shown. Further, in this specific embodiment, the probe 414 has a strain relief structure 434 with a tail 436 that extends proximally from the strain relief structure 434 as shown, with a proximal connector 437 disposed at the proximal end of the tail 436. In accordance with some embodiments, the probe 414 and the temperature sensing device 416 can be substantially similar to the probe 14 and temperature sensing device 16 discussed above in relation to FIGS. 1C and 1D. Further, in certain aspects, the connector box 420 and cables 424, 426 can be substantially similar to the connector box 20 and cables 24, 26 discussed above in relation to FIGS. 15A-15D.

In this specific embodiment, the system 410 also has a cable assembly 440 to which the proximal connector 437 is coupleable. The cable assembly 440 has a tail connector 442 to which the proximal connector 437 can couple and a set of cables 444A-E extending from the connector 442. When the proximal connector 437 is connected to the tail connector 442, each of the cables 444A-E can be operably coupled to a separate contact in the probe 414. As shown, the cable assembly 440 has five cables 444A-E such that the probe 414 can have up to five contacts. However, in the specific exemplary system 410 herein, the probe 414 has two contacts (not shown), and, as a result, only two cables 444A, 444B are needed. These specific two cables 444A-B are thus coupled to the connector box 420 as shown, thereby resulting in the probe 414—and specifically the two contacts (not shown) of the probe 414—being connected to the controller 412 via the connector box 420 and the controller interface box 422 as shown.

In use, this system 410 can be operated in substantially the same way as the system 10 discussed in further detail above, except as set forth herein. More specifically, the ablation probe 414 is first coupled to the system 410 by coupling the tail 436 to the cable assembly 440 and further by coupling the two cables relating to the two contacts (not shown) in the probe 414 (in this case, cables 444A-B) to the connector box 420. Once the probe 414 is coupled to the system 410, the probe 414 is then inserted into the brain of the patient and positioned as desired. Prior to ablation, the temperature sensing device 416 (with the appropriate spacer attached to ensure that the sensor or sensors are disposed adjacent to the contacts of the probe 414) is inserted into the lumen (not shown) in the ablation probe 414. Thus, the system 410 can be operated in a similar fashion as described above with respect to system 10 to provide for temperature feedback during ablation and real-time adjustment of the ablation energy based on that feedback.

In accordance with certain implementations, in place of a set of spacers of different sizes, an adjustable spacing device 450 as shown in FIGS. 22A and 22B can be used to ensure that the temperature sensing device 454 is positioned at the correct location within the probe 452. The probe 452 and temperature sensing device 454 are depicted schematically in these figures, and it is noted that any of the various probe and temperature sensing device embodiments disclosed or contemplated herein can operate in a similar fashion in relation to the adjustable spacing device 450.

In this embodiment as best shown in FIG. 22A, the device 450 has an outer body or tube 456 and an inner body or tube 458. The outer tube 456 has a lumen 460 defined therethrough with an inner diameter such that the inner tube 458 can be slidably positioned therein, as best shown in FIG. 22B. The outer tube 456 also has an opening or window 462 in the side of tube 456 such that the opening 462 provides visual access to the lumen 460 of the tube 456. The outer tube 456 has an outer diameter that is substantially similar to the outer diameter of the temperature sensing device 454 (or, more precisely, the portion of the temperature sensing device 454 that contacts the end of the outer tube 456 as shown).

The inner tube 458 has a lumen 464 defined therethrough such that the temperature sensing device can be positioned therethrough during use as described elsewhere herein. Further, the inner tube 458 has numbers or other markings 466 on the outer surface of the tube 458 that indicate the position of the tube 458 within the outer tube 456 via the opening 462 in the outer tube 456 and thereby indicate the resulting position of the temperature sensing device 454 within the probe 452. In addition, the inner tube 458 has an outer diameter that allows it to be positioned through the lumen 460 of the outer tube 456 as mentioned above and also is substantially similar to the outer diameter of the probe 452 (or, more precisely, the portion of the probe 452 that contacts the end of the inner tube 458 as shown).

In use, the spacer 450 can be attached at one end to the proximal end of the probe 452 in a fashion similar to that described elsewhere herein, thereby resulting in the inner tube 458 and probe 452 being coupled together such that the inner tube 458 cannot move axially in relation to the probe 452. At this point, the temperature sensing device 454 is attached to the opposite end of the spacer 450, thereby resulting in the outer tube 456 and the temperature sensing device 454 being coupled together such that the outer tube 456 cannot move axially in relation to the temperature sensing device 454. Alternatively, the spacer 450 can first be attached to the temperature sensing device 454 and then to the probe 452.

Once the spacer 450 is attached to both devices 452, 454, the spacer 450 can then be adjusted to the desired position such that the temperature sensing device 454 is disposed at the desired location in relation to the probe 452 and, as a result, the temperature sensors are disposed adjacent to the desired contacts in the probe 452, as discussed in detail elsewhere herein. That is, the inner tube 458 and the outer tube 456 are moved axially in relation to each other to the desired position, thereby resulting in the temperature sensing device 454 being moved axially in relation to the probe 452 to the desired position. Alternatively, the inner tube 458 and the outer tube 456 can be adjusted to their desired positions prior to attaching the probe 452 and the temperature sensing device 454.

As a result, the adjustable spacer 450 can be used to control the exact position of the distal end of the temperature sensing device 454 within the probe 452.

Figure 24:
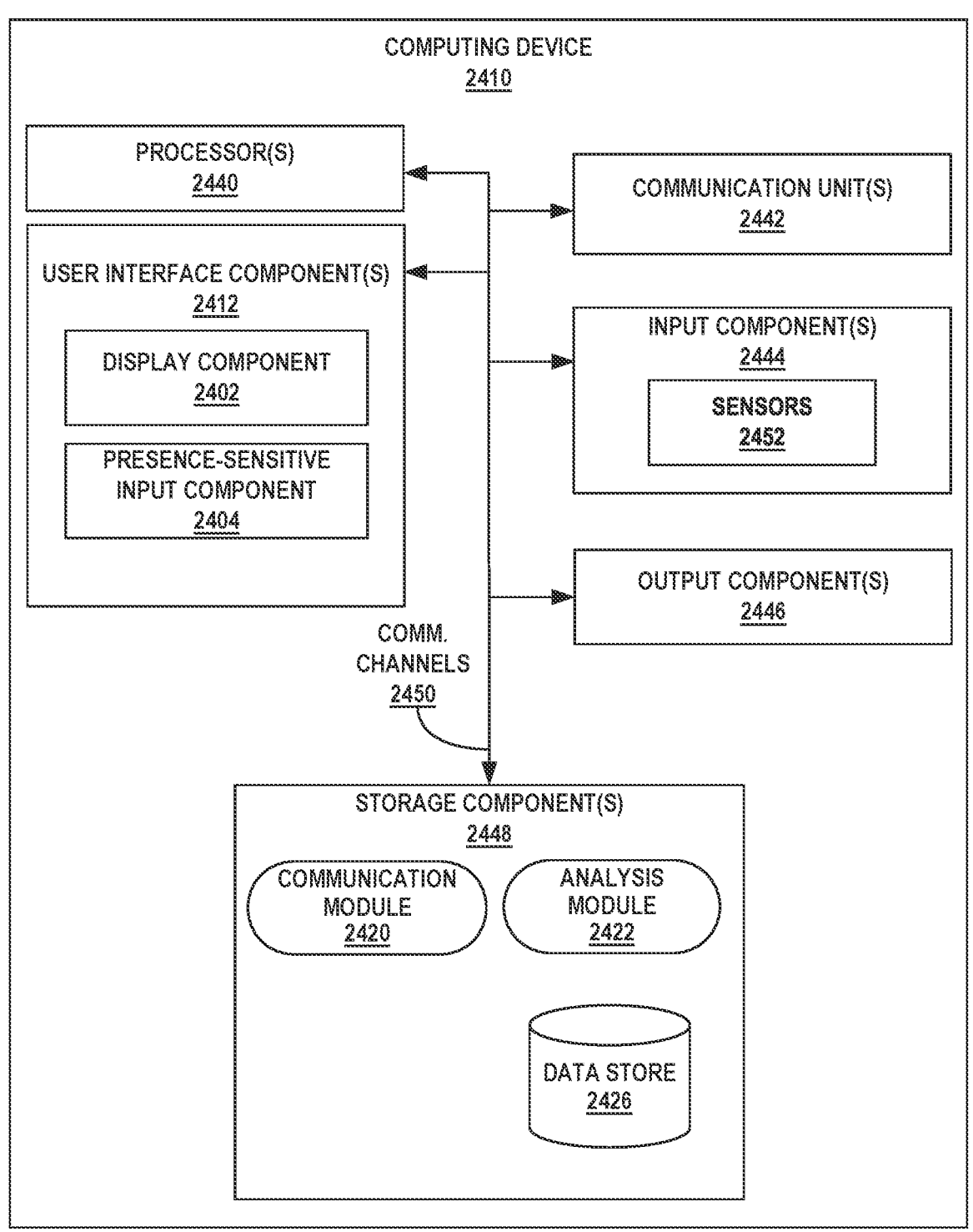
FIG. 24 is a schematic depiction of a computing system, according to one embodiment.

FIG. 24 is a block diagram illustrating a more detailed example of a computing device configured to perform the techniques described herein. Computing device 2410 of FIG. 24 is described below as an example of controller 12 of FIG. 1A or controller 412 of FIG. 21A. For instance, computing device 2410 may be controller 12 or controller 412, or computing device 2410 may contain a component (e.g., processors 2440) equivalent to controller 12 or controller 412. FIG. 24 illustrates only one particular example of computing device 2410, and many other examples of computing device 2410 may be used in other instances and may include a subset of the components included in example computing device 210 or may include additional components not shown in FIG. 24.

Computing device 2410 may be any computer with the processing power required to adequately execute the techniques described herein. For instance, computing device 2410 may be any one or more of a mobile computing device (e.g., a smartphone, a tablet computer, a laptop computer, etc.), a desktop computer, a smart component of a facility (e.g., a computerized device, a control panel for facility components, etc.), a vehicle, a wearable computing device (e.g., a smart watch, computerized glasses, a monitor, etc.), a virtual reality/augmented reality/extended reality (VR/AR/XR) system, a streaming system, a network modem, router, or server system, or any other computerized device that may be configured to perform the techniques described herein.

As shown in the example of FIG. 24, computing device 2410 includes user interface components (UIC) 2412, one or more processors 2440, one or more communication units 242, one or more input components 2444, one or more output components 2446, and one or more storage components 2448. UIC 2412 includes display component 2402 and presence-sensitive input component 2404. Storage components 2448 of computing device 210 include communication module 2420, analysis module 2422, and data store 2426.

One or more processors 2440 may implement functionality and/or execute instructions associated with computing device 2410 to receive temperature information from a temperature sensing device (e.g., temperature sensing device 16 of FIG. 1 or any other temperature sensing device according to any embodiment herein) and use the temperature information to adjust energy supply to at least one of the at least two electrode contacts (e.g., an electrode contact present on a probe, such as probe 14 of FIG. 1 or any other electrode device according to any embodiment herein). That is, processors 240 may implement functionality and/or execute instructions associated with computing device 210 to analyze temperature information in order to control energy supply to electrode contacts near the temperature sensing device.

Examples of processors 2440 include any combination of application processors, display controllers, auxiliary processors, one or more sensor hubs, and any other hardware configured to function as a processor, a processing unit, or a processing device, including dedicated graphical processing units (GPUs). Modules 2420 and 2422 may be operable by processors 2440 to perform various actions, operations, or functions of computing device 210. For example, processors 2440 of computing device 2410 may retrieve and execute instructions stored by storage components 2448 that cause processors 240 to perform the operations described with respect to modules 2420 and 2422. The instructions, when executed by processors 2440, may cause computing device 2410 to receive temperature information from a temperature sensing device and use the temperature information to adjust energy supply to at least one of the at least two electrode contacts.

Communication module 2420 may execute locally (e.g., at processors 2440) to provide functions associated with communicating with temperature sensing devices and probes with electrode contacts. In some examples, communication module 2420 may act as an interface to a remote service accessible to computing device 2410. For example, communication module 2420 may be an interface or application programming interface (API) to a remote server that receives information from temperature sensing devices and outputs commands to probes and/or electrode contacts.

In some examples, analysis module 2422 may execute locally (e.g., at processors 2440) to provide functions associated with analyzing temperature information and determining whether more energy or less energy should be supplied to electrode contacts. In some examples, analysis module 2422 may act as an interface to a remote service accessible to computing device 2410. For example, analysis module 2422 may be an interface or application programming interface (API) to a remote server that analyzes the received temperature information and determines the appropriate energy levels for the electrode contacts.

One or more storage components 2448 within computing device 2410 may store information for processing during operation of computing device 2410 (e.g., computing device 2410 may store data accessed by modules 2420 and 2422 during execution at computing device 2410). In some examples, storage component 2448 is a temporary memory, meaning that a primary purpose of storage component 2448 is not long-term storage. Storage components 2448 on computing device 2410 may be configured for short-term storage of information as volatile memory and therefore not retain stored contents if powered off. Examples of volatile memories include random access memories (RAM), dynamic random access memories (DRAM), static random access memories (SRAM), and other forms of volatile memories known in the art.

Storage components 2448, in some examples, also include one or more computer-readable storage media. Storage components 2448 in some examples include one or more non-transitory computer-readable storage mediums. Storage components 2448 may be configured to store larger amounts of information than typically stored by volatile memory. Storage components 2448 may further be configured for long-term storage of information as non-volatile memory space and retain information after power on/off cycles. Examples of non-volatile memories include magnetic hard discs, optical discs, floppy discs, flash memories, or forms of electrically programmable memories (EPROM) or electrically erasable and programmable (EEPROM) memories. Storage components 2448 may store program instructions and/or information (e.g., data) associated with modules 2420 and 2422 and data store 2426. Storage components 2448 may include a memory configured to store data or other information associated with modules 2420 and 2422 and data store 2426.

Communication channels 2450 may interconnect each of the components 2412, 2440, 2442, 2444, 2446, and 2448 for inter-component communications (physically, communicatively, and/or operatively). In some examples, communication channels 2450 may include a system bus, a network connection, an inter-process communication data structure, or any other method for communicating data.

One or more communication units 2442 of computing device 2410 may communicate with external devices via one or more wired and/or wireless networks by transmitting and/or receiving network signals on one or more networks. Examples of communication units 2442 include a network interface card (e.g., such as an Ethernet card), an optical transceiver, a radio frequency transceiver, a GPS receiver, a radiofrequency identification (RFID) transceiver, a near-field communication (NFC) transceiver, or any other type of device that can send and/or receive information. Other examples of communication units 2442 may include short wave radios, cellular data radios, wireless network radios, as well as universal serial bus (USB) controllers.

One or more input components 2444 of computing device 2410 may receive input. Examples of input are tactile, audio, and video input. Input components 2444 of computing device 2410, in one example, include a presence-sensitive input device (e.g., a touch sensitive screen, a PSD), mouse, keyboard, voice responsive system, camera, microphone or any other type of device for detecting input from a human or machine. In some examples, input components 2444 may include one or more sensor components (e.g., sensors 2452). Sensors 2452 may include one or more biometric sensors (e.g., fingerprint sensors, retina scanners, vocal input sensors/microphones, facial recognition sensors, cameras), one or more location sensors (e.g., GPS components, Wi-Fi components, cellular components), one or more temperature sensors, one or more movement sensors (e.g., accelerometers, gyros), one or more pressure sensors (e.g., barometer), one or more ambient light sensors, and one or more other sensors (e.g., infrared proximity sensor, hygrometer sensor, and the like). Other sensors, to name a few other non-limiting examples, may include a radar sensor, a lidar sensor, a sonar sensor, a heart rate sensor, magnetometer, olfactory sensor, compass sensor, or a step counter sensor.

One or more output components 2446 of computing device 2410 may generate output in a selected modality. Examples of modalities may include a tactile notification, audible notification, visual notification, machine generated voice notification, or other modalities. Output components 2446 of computing device 2410, in one example, include a presence-sensitive display, a sound card, a video graphics adapter card, a speaker, a cathode ray tube (CRT) monitor, a liquid crystal display (LCD), a light emitting diode (LED)

display, an organic LED (OLED) display, a virtual/augmented/extended reality (VR/AR/XR) system, a three-dimensional display, or any other type of device for generating output to a human or machine in a selected modality.

UIC 2412 of computing device 2410 includes display component 2402 and presence-sensitive input component 2404. UIC 2412 may be configured to output one or more graphical user interfaces, such as interactive interface 18 of FIG. 1A or interactive interface 418 of FIG. 21A. Display component 2402 may be a screen, such as any of the displays or systems described with respect to output components 2446, at which information (e.g., a visual indication) is displayed by UIC 2412 while presence-sensitive input component 2404 may detect an object at and/or near display component 2402.

While illustrated as an internal component of computing device 2410, UIC 2412 may also represent an external component that shares a data path with computing device 2410 for transmitting and/or receiving input and output. For instance, in one example, UIC 2412 represents a built-in component of computing device 2410 located within and physically connected to the external packaging of computing device 2410 (e.g., a screen on a mobile phone). In another example, UIC 2412 represents an external component of computing device 2410 located outside and physically separated from the packaging or housing of computing device 2410 (e.g., a monitor, a projector, etc. that shares a wired and/or wireless data path with computing device 2410).

UIC 2412 of computing device 2410 may detect two-dimensional and/or three-dimensional gestures as input from a user of computing device 2410. For instance, a sensor of UIC 2412 may detect a user's movement (e.g., moving a hand, an arm, a pen, a stylus, a tactile object, etc.) within a threshold distance of the sensor of UIC 2412. UIC 2412 may determine a two or three-dimensional vector representation of the movement and correlate the vector representation to a gesture input (e.g., a hand-wave, a pinch, a clap, a pen stroke, etc.) that has multiple dimensions. In other words, UIC 2412 can detect a multi-dimension gesture without requiring the user to gesture at or near a screen or surface at which UIC 2412 outputs information for display. Instead, UIC 2412 can detect a multi-dimensional gesture performed at or near a sensor which may or may not be located near the screen or surface at which UIC 2412 outputs information for display.

In accordance with the techniques of this disclosure, communication module 2420 may receive temperature information from a temperature sensing device, such as temperature sensing device 16 of FIG. 1A, temperature sensing device 416 of FIG. 21A, or any other temperature sensing device according to any other embodiment herein. Analysis module 2422 may analyze the temperature information to determine whether the patient and/or an ablation probe (e.g., ablation probe 14 of FIG. 1A, probe 414 of FIG. 21A, or any other electrode device according to any embodiment herein) is too warm or too cold during the course of normal operation and treatment. If analysis module 2422 determines that the temperature is outside of the proper range of temperatures, analysis module 2422 may determine that the energy supply provided to the ablation probe and the electrode contacts on the ablation probe should be adjusted to bring the temperature back within the proper range. Communication module 2420 may send commands either directly to ablation probe or to a radiofrequency generator (such as generator 28 as best shown schematically in FIG. 1B, generator 428 as shown in FIG. 21B, or any other such generator as disclosed or contemplated herein) that provides the ablation energy to the ablation probe in order to increase or decrease the amount of ablation energy received by ablation probe, thereby increasing or decreasing the temperature at the temperature sensing device.

Thus, computing device 2410 and/or controller 12 or controller 412 work with the system 10 provides for temperature feedback during ablation and real-time adjustment of the ablation energy based on that feedback. Computing device 2410 may be integrated with the particular external devices of the temperature sensing device and the ablation probe in order to control such devices in the improved treatment of a patient receiving therapy from the ablation probe.

Although the various examples have been described with reference to preferred implementations, persons skilled in the art will recognize that changes may be made in form and detail without departing from the spirit and scope thereof.

It is to be recognized that depending on the example, certain acts or events of any of the techniques described herein can be performed in a different sequence, may be added, merged, or left out altogether (e.g., not all described acts or events are necessary for the practice of the techniques). Moreover, in certain examples, acts or events may be performed concurrently, e.g., through multi-threaded processing, interrupt processing, or multiple processors, rather than sequentially.

In one or more examples, the functions described may be implemented in hardware, software, firmware, or any combination thereof. If implemented in software, the functions may be stored on or transmitted over as one or more instructions or code on a computer-readable medium and executed by a hardware-based processing unit. Computer-readable media may include computer-readable storage media, which corresponds to a tangible medium such as data storage media, or communication media including any medium that facilitates transfer of a computer program from one place to another, e.g., according to a communication protocol. In this manner, computer-readable media generally may correspond to (1) tangible computer-readable storage media which is non-transitory or (2) a communication medium such as a signal or carrier wave. Data storage media may be any available media that can be accessed by one or more computers or one or more processors to retrieve instructions, code and/or data structures for implementation of the techniques described in this disclosure. A computer program product may include a computer-readable medium.

By way of example, and not limitation, such computer-readable storage media can comprise RAM, ROM, EEPROM, CD-ROM or other optical disk storage, magnetic disk storage, or other magnetic storage devices, flash memory, or any other medium that can be used to store desired program code in the form of instructions or data structures and that can be accessed by a computer. Also, any connection is properly termed a computer-readable medium. For example, if instructions are transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. It should be understood, however, that computer-readable storage media and data storage media do not include connections, carrier waves, signals, or other transitory media, but are instead directed to non-transitory, tangible storage media. Disk and disc, as used herein, includes compact disc (CD), laser disc, optical disc, digital versatile disc (DVD), floppy disk and Blu-ray disc, where disks usually reproduce data magnetically, while discs reproduce data optically with lasers. Combinations of the above should also be included within the scope of computer-readable media.

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor," as used herein may refer to any of the foregoing structure or any other structure suitable for implementation of the techniques described herein. In addition, in some aspects, the functionality described herein may be provided within dedicated hardware and/or software modules configured for encoding and decoding, or incorporated in a combined codec. Also, the techniques could be fully implemented in one or more circuits or logic elements.

The techniques of this disclosure may be implemented in a wide variety of devices or apparatuses, including a wireless handset, an integrated circuit (IC) or a set of ICs (e.g., a chip set). Various components, modules, or units are described in this disclosure to emphasize functional aspects of devices configured to perform the disclosed techniques, but do not necessarily require realization by different hardware units. Rather, as described above, various units may be combined in a codec hardware unit or provided by a collection of interoperative hardware units, including one or more processors as described above, in conjunction with suitable software and/or firmware.

While the various systems described above are separate implementations, any of the individual components, mechanisms, or devices, and related features and functionality, within the various system embodiments described in detail above can be incorporated into any of the other system embodiments herein.

The terms "about" and "substantially," as used herein, refers to variation that can occur (including in numerical quantity or structure), for example, through typical measuring techniques and equipment, with respect to any quantifiable variable, including, but not limited to, mass, volume, time, distance, wave length, frequency, voltage, current, and electromagnetic field. Further, there is certain inadvertent error and variation in the real world that is likely through differences in the manufacture, source, or precision of the components used to make the various components or carry out the methods and the like. The terms "about" and "substantially" also encompass these variations. The term "about" and "substantially" can include any variation of 5% or 10%, or any amount—including any integer—between 0% and 10%. Further, whether or not modified by the term "about" or "substantially," the claims include equivalents to the quantities or amounts.

Numeric ranges recited within the specification are inclusive of the numbers defining the range and include each integer within the defined range. Throughout this disclosure, various aspects of this disclosure are presented in a range format. It should be understood that the description in range format is merely for convenience and brevity and should not be construed as an inflexible limitation on the scope of the disclosure. Accordingly, the description of a range should be considered to have specifically disclosed all the possible sub-ranges, fractions, and individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6, and decimals and fractions, for example, 1.2, 3.8, 1½, and 4¾ This applies regardless of the breadth of the range. Although the various embodiments have been described with reference to preferred implementations, persons skilled in the art will recognize that changes may be made in form and detail without departing from the spirit and scope thereof.

Although the various embodiments have been described with reference to preferred implementations, persons skilled in the art will recognize that changes may be made in form and detail without departing from the spirit and scope thereof.

What is claimed is:

1. A electrode probe and temperature sensor system comprising:

(a) an electrode device comprising an elongate tubular electrode body, the tubular electrode body comprising:

(i) at least two electrode contacts disposed on the elongate tubular electrode body;

(ii) a first lumen defined within the elongate tubular electrode body; and (iii) a proximal opening disposed near a proximal end of the elongate tubular electrode body, wherein the proximal opening is in fluidic communication with the first lumen; and (b) a temperature sensing device sized to be positionable within the first lumen, the temperature sensing device comprising:

(i) an elongate core body; and (ii) a thin film body disposed around the elongate core body, the thin film body comprising:

(A) an elongate base;

(B) at least two temperature sensors disposed on a top surface of the elongate base;

(C) an elongate common trace disposed on the top surface of the elongate base, wherein the elongate common trace is electrically coupled to the at least two temperature sensors; and (D) at least two elongate separate traces disposed on a bottom surface of the elongate base, wherein each of the at least two elongate separate traces is electrically coupled to one of the at least two temperature sensors.

2. The electrode probe and temperature sensor system of claim 1, wherein the thin film body further comprises at least two vias disposed through the elongate base, wherein each of the two vias electrically couples one of the at least one temperature sensors to one of the at least two elongate separate traces.

3. The electrode probe and temperature sensor system of claim 1, wherein the thin film body is a thin film ribbon disposed around the elongate core body in a helical configuration.

4. A electrode probe and temperature sensor system comprising:

(a) an electrode device comprising an elongate tubular electrode body, the tubular electrode body comprising:

(i) at least two electrode contacts disposed on the elongate tubular electrode body;

(ii) a first lumen defined within the elongate tubular electrode body; and (iii) a proximal opening disposed near a proximal end of the elongate tubular electrode body, wherein the proximal opening is in fluidic communication with the first lumen; and (b) a temperature sensing device sized to be positionable within the first lumen, the temperature sensing device comprising a thin film body disposed around a core body, the thin film body comprising:

(i) a base;

(ii) at least two temperature sensors disposed on a top surface of the base;

(iii) a common elongate conductor electrically coupled to the at least two temperature sensors; and (iv) at least two separate elongate conductors disposed on a bottom surface of the base, wherein each of the at least two separate elongate conductors is electrically coupled to one of the at least two temperature sensors.

5. The system of claim 4, wherein the temperature sensing device further comprises a proximal connector disposed at or near a proximal end of the thin film body.

6. The system of claim 5, wherein the common elongate conductor extends from the at least two temperature sensors to the proximal connector.

7. The system of claim 5, wherein each of the at least two separate elongate conductors extends from one of the at least two temperatures sensors to the proximal connector.

8. The system of claim 4, wherein the thin film body further comprises at least two vias disposed through the base, wherein each of the at least two vias electrically couples one of the at least one temperature sensors to one of the at least two separate elongate conductors.

9. The system of claim 4, wherein the thin film body is a thin film ribbon disposed around the elongate core body in a helical configuration.

10. The system of claim 4, wherein the at least two temperature sensors are spaced along the thin film body such that each of the at least two temperature sensors is disposed in proximity with one of the at least two electrode contacts when the temperature sensing device is positioned within the first lumen.

11. The system of claim 4, further comprising a controller operably coupled to the electrode device and the temperature sensing device, wherein the controller is configured to receive temperature information from the temperature sensing device and use the temperature information to adjust energy supply to at least one of the at least two electrode contacts.

12. The system of claim 4, further comprising at least one spacing device removably coupleable at a first end with the proximal end of the elongate tubular electrode body and at a second end with the temperature sensing device.

13. An ablation system comprising:

(a) an ablation device comprising:

(i) an elongate electrode body;

(ii) at least two electrode contacts disposed on the elongate electrode body; and (iii) a first lumen defined within the elongate electrode body;

(b) a temperature sensing device sized to be positionable within the first lumen, the temperature sensing device comprising:

(i) a core body;

(ii) a thin film body disposed around the core body, the thin film body comprising:

(A) a base layer;

(B) at least two temperature sensors disposed on a top surface of the base layer;

(C) a common elongate conductor electrically coupled to the at least two temperature sensors; and (D) at least two separate elongate conductors disposed on a bottom surface of the base layer, wherein each of the at least two separate elongate conductors is electrically coupled to one of the at least two temperature sensors, wherein the temperature sensing device is positionable within the first lumen such that each of the at least two temperature sensors is disposed in proximity with one of the at least two electrode contacts;

(c) at least one spacing device removably coupleable at a first end with the ablation device and at a second end with the temperature sensing device; and (d) a controller operably coupled to the electrode device and the temperature sensing device, wherein the controller is configured to receive temperature information from the temperature sensing device and use the temperature information to adjust energy supply to at least one of the at least two electrode contacts.

14. The system of claim 13, wherein the at least one spacing device comprises an adjustable spacing device.

15. The system of claim 14, wherein the adjustable spacing device comprises:

(a) an elongate tubular spacing body comprising:

(i) a spacing body lumen defined within the elongate tubular spacing body;

(ii) an opening defined in the elongate tubular spacing body, wherein the opening is in visual communication with the spacing body lumen; and (iii) an end of the elongate tubular spacing body coupleable with the temperature sensing device such that the elongate tubular spacing body is axially constrained to the temperature sensing device; and (b) an elongate tubular insert body slidably disposed within the spacing body lumen, the elongate tubular insert body comprising:

(i) an insert body lumen defined within the elongate tubular insert body;

(ii) a plurality of markings on an external surface of the elongate tubular insert body such that the plurality of markings are visible through the opening defined in the elongate tubular spacing body; and (iii) an end of the elongate tubular insert body coupleable with the ablation device such that the elongate tubular insert body is axially constrained to the ablation device.

16. The system of claim 13, wherein the at least one spacing device comprises:

(a) an elongate tubular spacing body;

(b) a spacing device lumen defined within the elongate tubular spacing body; and (c) an elongate opening defined along a length of the elongate tubular spacing body, wherein the elongate opening is in fluidic communication with the spacing device lumen, wherein the at least one spacing device is attachable to and detachable from the temperature sensing device via the elongate opening.

17. The system of claim 13, wherein the at least one spacing device comprises a plurality of spacing devices, wherein each of the plurality of spacing devices has a different length in comparison to every other of the plurality of spacing devices, wherein a desired spacing device can be selected from the plurality of the spacing devices such that the at least two temperature sensors are disposed in proximity with a desired one of the at least two electrode contacts.

18. The system of claim 13, wherein the thin film body further comprises at least two vias disposed through the base, wherein each of the at least two vias electrically couples one of the at least one temperature sensors to one of the at least two separate elongate conductors.

19. The system of claim 13, wherein the at least two temperature sensors are spaced along the thin film body such that each of the at least two temperature sensors is disposed in proximity with one of the at least two electrode contacts when the temperature sensing device is positioned within the first lumen.

20. The system of claim 13, wherein the thin film body is a thin film ribbon disposed around the core body in a helical configuration.

* * * * *